United States Patent
Qiu et al.

(10) Patent No.: US 12,257,016 B2
(45) Date of Patent: Mar. 25, 2025

(54) MAGNETIC FIELD GENERATOR

(71) Applicant: MAX-PLANCK-GESELLSCHAFT ZUR FÖRDERUNG DER WISSENSCHAFTEN E.V., Munich (DE)

(72) Inventors: Tian Qiu, Stuttgart (DE); Peer Fischer, Freiburg (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 857 days.

(21) Appl. No.: 17/054,779

(22) PCT Filed: May 18, 2018

(86) PCT No.: PCT/EP2018/063105
§ 371 (c)(1),
(2) Date: Nov. 12, 2020

(87) PCT Pub. No.: WO2019/219207
PCT Pub. Date: Nov. 21, 2019

(65) Prior Publication Data
US 2021/0228298 A1 Jul. 29, 2021

(51) Int. Cl.
*H01F 7/02* (2006.01)
*A61B 34/00* (2016.01)

(52) U.S. Cl.
CPC ........... *A61B 34/73* (2016.02); *H01F 7/0221* (2013.01); *A61B 2034/732* (2016.02)

(58) Field of Classification Search
CPC .............................. H01F 7/0221; A61B 34/73
USPC .......................................................... 335/306
See application file for complete search history.

(56) References Cited

U.S. PATENT DOCUMENTS

| 6,157,853 A | 12/2000 | Blume et al. |
| 6,311,082 B1 * | 10/2001 | Creighton, IV ....... A61B 34/73 600/407 |
| 6,537,196 B1 | 3/2003 | Creighton, IV et al. |
| 7,479,859 B2 * | 1/2009 | Gerber .................... H01F 13/00 209/217 |

(Continued)

FOREIGN PATENT DOCUMENTS

| CN | 1944003 A | 4/2007 |
| EP | 1030589 | 8/2000 |

(Continued)

OTHER PUBLICATIONS

Patrick Ryan et al., Five-Degree-of-Freedom Magnetic Control of Micro-Robots Using Rotating Permanent Magnets, 2016 IEEE International Conference on Robotics and Automation (ICRA), May 16-21, 2016, pp. 1731-1736.

(Continued)

*Primary Examiner* — Alexander Talpalatski

(57) ABSTRACT

A magnetic field generator that comprises at least three groups of magnets, the magnetic moment of each magnet being rotatable about a rotation axis, wherein each group comprises at least two magnets, and each group has an orientation in the sense that the rotation axes of the magnetic moments of the magnets of the same group extend in the group's orientation. The orientations of the different groups are linearly independent.

10 Claims, 20 Drawing Sheets

(56) References Cited

U.S. PATENT DOCUMENTS

| | | | |
|---|---|---|---|
| 7,986,205 B2* | 7/2011 | Horisaka | A61B 34/70 324/319 |
| 8,830,648 B2* | 9/2014 | Abbott | A61B 34/70 361/139 |
| 10,004,566 B2* | 6/2018 | Park | A61B 34/73 |
| 10,283,009 B2* | 5/2019 | Lee | G01M 99/00 |
| 2006/0114088 A1* | 6/2006 | Shachar | A61B 5/7455 335/219 |
| 2008/0016677 A1 | 1/2008 | Creighton, IV | |
| 2014/0148643 A1 | 5/2014 | Kawano | |
| 2019/0184545 A1* | 6/2019 | Jang | A61B 34/73 |

FOREIGN PATENT DOCUMENTS

| | | |
|---|---|---|
| EP | 1156739 | 11/2001 |
| EP | 1168974 | 1/2002 |
| EP | 2036483 A1 | 3/2009 |
| JP | 2010029350 A | 2/2010 |
| WO | 2014108303 A1 | 7/2014 |

OTHER PUBLICATIONS

Wei Zhang et al., A Novel Method of Arraying Permanent Magnets Circumferentially to Generate a Rotation Magnetic Field, IEEE Transactions on Magnetics, Oct. 2008, pp. 2367-2372, vol. 44, No. 10.

Herbert A. Leupold et al., Novel High Field Permanent Magnet Flux Sources, IEEE Transactions on Magnetics, Sep. 1987, pp. 1-3, vol. 23, No. 5.

International Search Report of PCT Patent Application No. PCT/EP2018/063105 issued on Mar. 15, 2019.

* cited by examiner

MAGNETIC FIELD GENERATOR

FIELD OF THE INVENTION

The invention relates to a magnetic field generator. The invention further relates to a method of changing at least one property of a resulting magnetic field generated by magnets. Finally, the invention relates to a use of the magnetic field generators and the methods.

BACKGROUND OF THE INVENTION

It is desirable to generate a magnetic field that has a high flux density and an arbitrarily controlled direction in a three-dimensional workspace, while keeping the workspace accessible. Three approaches are normally used to generate a magnetic field:

A magnetic field can be generated by electromagnetic coils. The field strength and direction can be easily controlled by the electric current that runs through the coil. Typical examples are Helmholtz coils and Maxwell coils. However, electromagnets can suffer from many practical drawbacks: a) Joule heating leads to a rise in temperature in the coils (and hence their resistance) and a temperature increase in the surrounding working space, thus cumbersome cooling systems are often required; furthermore b) coil designs to achieve large fields are heavy and electric amplifiers, that are needed to drive them, are expensive; and c) the field strength is limited and does not scale easily to accommodate a larger working space enclosed by the coils (eg to accommodate a human).

An alternative approach is to use a superconducting magnetic coil, such as the one used in MRI machines. It can generate very high field strength (0.2 to 9 T), however, the direction and magnitude of the field are not easily variable, and they require cryogenic cooling systems.

A third approach is to arrange permanent magnets in a way that the fields generated by each magnet superimpose to yield a stronger field. By mechanically changing the orientation and/or position of each magnet, the direction of the superimposed field can be varied. Compared with electromagnetic and superconducting coils, permanent magnets do not require any electric current, which eliminates the heating and cooling problem. However, changing the orientation or position of the magnets requires mechanical rotation or translation, which may cause vibrations, and more severely, the mechanical movement of the magnets limits access to the workspace, ie access to the volume enclosed by the magnets can be constrained (or even completely blocked). Taking medical application as an example, a constrained workspace means that patients' position and orientation is limited, medical instruments, including tools, electric wires and tubes, cannot reach the patient, and optical paths are blocked so that observation and imaging is obscured.

P Ryan and E Diller in "Five-Degree-of-Freedom Magnetic Control of Micro-Robots Using Rotating Permanent Magnets", 2016 IEEE International Conference on Robotics and Automation (ICRA), Stockholm, Sweden, 16 to 21 May 2016, describe a system of eight rotatable permanent magnets for creating fields and gradients in any direction. Each magnet is rotatable about an axis that extends in a direction perpendicular to the magnet's magnetic moment. The positions of the magnets and the orientations of the rotation axes were obtained by maximizing a metric that represents the average magnetic field and gradient as well as their standard deviations. The authors used their system to control the path of a 250 μm micro-magnet.

W Zhang et al in "A Novel Method of Arraying Permanent Magnets Circumferentially to Generate a Rotation Magnetic Field", IEEE Transactions on Magnetics, Vol 44, No 10, October 2008, disclose an array of six magnets equidistantly arranged in a circle. The magnets are rotatable about axes that extend parallel to the axis of the circle and the magnets' magnetic moments extend in a direction perpendicular to the axes of rotation. All of the magnets rotate in the same direction synchronously, generating a constant strength and reverse rotation magnetic field in the centre area of the circle.

H A Leupold and E Potenziani in "Novel High-Field Permanent Magnet Flux Sources" describe several compact permanent-magnet configurations that produce fields greater than the remanence of the magnetic material comprising them. The configurations are based on Halbach hollow cylindrical flux source (HCFS) and hollow spherical flux source (HSFS) principles.

From U.S. Pat. No. 6,537,196 B1 an adjustable field magnet assembly is known that comprises at least two magnets rotatably mounted so that the rotation of at least one of the magnets changes the magnetic field projected by the magnet assembly. The intended use of the assembly is to provide a magnet field of variable direction for use in magnetically navigating medical objects in the body by rotating the magnets comprising the assembly and/or rotating the entire assembly. Other assemblies of magnets are disclosed in U.S. Pat. No. 6,157,853, US 2008/016677 A1, EP 1156739 A2, EP 1168974 A1 and EP 1030589 A2.

OBJECT OF THE INVENTION

It is an object of the present invention to provide an improved magnetic field generator. Moreover, the present invention aims at providing an improved method of changing at least one property of a resulting magnetic field generated by magnets. Finally, it is an object of the present invention to provide a use of the magnetic field generator and the method.

Solution According to the Invention

The reference numerals in the patent claims are not meant to be limiting but merely serve to improve readability of the claims.

In one aspect of the invention the problem is solved by a magnetic field generator according to claim 1. The magnetic field generator comprises at least three groups of magnets, the magnetic moment of each magnet being rotatable about a rotation axis. Each group comprises at least two magnets, and each group has an orientation in the sense that the rotation axes of the magnetic moments of the magnets of the same group extend in the group's orientation. Moreover, the orientations of the different groups are linearly independent.

In the context of the present invention "linearly independent" with reference to a set of orientations means that no vector with one of the orientations of the set of orientations can be defined as a linear combination of vectors each with one of the other orientations of the set of orientations.

In the context of the present invention the requirement that the magnetic moments extend "in the group's orientation" means that there exists an orientation ("the group's orientation") in relation to which each of the rotation axes of the magnetic moments of the magnets of the group is inclined by less than 15 degrees (provided that a full circle comprises 360 degrees), preferably less than 10 degrees, more preferably less than 5 degrees, even more preferably less than 1 degree. In the following, if not otherwise stated, the term "group" always refers to a group with an orientation in the above sense.

According to an related aspect of the invention the problem is solved by a method of changing at least one property of a resulting magnetic field generated by magnets according to claim 9. The resulting magnetic field is generated by at least three groups of magnets by means of rotating the magnetic moment of each magnet about a rotation axis. Each group comprises at least two magnets, and each group has an orientation in the sense that the rotation axis of the magnetic moments of the magnets of the same group extend in the groups orientation. The orientations of the different groups are linearly independent.

In another aspect of the invention the problem is solved by a magnetic field generator according to claim 2. The magnetic field generator comprises at least six magnets, and input means for a set of control parameters. The magnetic moment of each magnet is rotatable about a rotation axis such that in a workspace the magnetic fields of the magnets in combination can generate a resulting magnetic field of arbitrary orientation and arbitrary flux density. The orientation and flux density of the resulting magnetic field is determined by the values of less than six control parameters.

A "control parameter" in the sense of the present invention is a scaler. In other words, the control parameter has a single numeric value. The value of the control parameter can be provided to the magnetic field generator in any suitable form, for example as the magnitude of a voltage or as an electrical signal that encodes the value of the control parameter in a digital form.

A "workspace" in the meaning of the present invention is a three-dimensional volume of space. The "resulting magnetic field" is the magnetic field in the workspace. The orientation and flux density of the resulting magnetic field can vary as a function of location within the workspace. Accordingly, in the context of the present invention the "orientation and flux density" of the resulting magnetic field means the arithmetic mean orientation and arithmetic mean flux density of the magnetic field in the workspace. Likewise, the spatial gradient of the flux density (referred to further below) of the resulting magnetic field means the arithmetic mean spatial gradient of the flux density in the workspace.

In the context of the present invention, "arbitrary orientation" with regard to the resulting magnetic field means any orientation in three-dimensional space. "Arbitrary flux density" with regard to the resulting magnetic field means any flux density between 0 and a maximum achievable flux density. The maximum achievable flux density of the resulting magnetic field in some embodiments of the invention varies as a function of the orientation of the resulting magnetic field. It is determined by the details of the construction of the magnetic field generator such as the position and magnetic moment of the magnets. Therefore, according to this aspect of the invention, the resulting magnetic field can assume any orientation in three dimensional space and any flux density between 0 and the a maximum achievable flux density specific to the respective orientation.

The requirement that the "arbitrary orientation and arbitrary flux density is determined by the values of the control parameters" means that for any combination of orientation and flux density there exists at least one set of values of the control parameters that when input to the magnetic field generator prompt the generator to generate a resulting magnetic field at the location of the workspace that has this combination of orientation and flux density. In other words, each set of values of control parameters unambiguously determines the orientation and flux density of the resulting magnetic field.

In a related aspect of the present invention the problem is solved by a method of changing at least one property of a resulting magnetic field generated by magnets wherein the resulting magnetic field is generated by at least six magnets by means of rotating the magnetic moment of each magnet about a rotation axis. The resulting magnetic field can have arbitrary orientation and arbitrary flux density. The orientation and flux density of the resulting magnetic field is determined by setting the angle of rotation of the magnetic moments about the respective rotational axes to values derived from the values of a set of less than six control parameters.

In another aspect of the invention, the problem is solved by a magnetic field generator with the features of claim 3. The magnetic field generator comprises at least two groups of magnets, the magnetic moment of each magnet being rotatable about a rotation axis. Each group comprises at least two magnets, and each group has an orientation in the sense that the rotation axes of the magnetic moments of the magnets of the same group extend in the group's orientation. The magnets of the same group are operationally coupled with regard to the rotation of their magnetic moments such that their magnetic moments rotate simultaneously by identical angles about their respective rotation axis.

In the context of the present invention "simultaneously by identical angles" means that the magnetic moments rotate at the same time and with the same angular velocity. It does not mean that the magnetic moments necessarily rotate in the same direction (the direction being clockwise or counterclockwise). It also does not mean that they necessarily rotate from the same starting angle; rather, the angles of rotation of the magnetic moments may be offset relatively to each other.

In a related aspect of the invention the problem is solved by a method of changing at least one property of a resulting magnetic field generated by magnets wherein the field is generated by at least two groups of magnets by means of rotating the magnetic moment of each magnet about a rotation axis. Each group comprises at least two magnets, and each group has an orientation in the sense that the rotation axes of the magnetic moments of the magnets of the same group extend in the group's orientation. The magnets of the same group rotate simultaneously by identical angles about their respective rotation axis.

In another aspect of the invention the problem is solved by a magnetic field generator with the features of claim 4. The magnetic field generator comprises at least two groups of magnets, the magnetic moment of each magnet being rotatable about a rotation axis. Each group comprises at least two magnets, and each group has an orientation in the sense that the rotation axes of the magnetic moments of the magnets of the same group extend in the group's orientation. The magnets are located on the edges of a parallelepiped, or on intersecting circles located on a sphere.

In other words, there exists a parallelepiped that for each magnet has an edge on which the magnet is essentially located, or there exist intersecting circumferences on the surface of an ellipsoid and the magnets are located essentially on the circumferences. "Circumferences" of an ellipsoid are all curves the geometrical centre of which coincides with the geometrical centre of the ellipsoid. The expression "intersecting circumferences means that each circumference intersects with each other circumference that has a magnet located essentially on it. The requirement that a magnet is located "essentially" on an edge or a circumference means that distance between the edge or the circumference and the magnet is less than 15% of the length of the edge or the mean diameter of the circumference, respectively.

In a related aspect of the invention the problem is solved by a method of changing at least one property of a resulting magnetic field. The field is generated by at least two groups of magnets by means of rotating the magnetic moment of each magnet about a rotation axis. Each group comprises at least two magnets, and each group has an orientation in the sense that the rotation axes the magnetic moments of the magnets of the same group extend in the group's orientation. The magnets are located essentially on the edges of a parallelepiped, or essentially on intersecting circumferences on an ellipsoid.

It is an achievable advantage of the magnetic field generators and the methods according to the invention that in a workspace the magnetic fields of the magnets in combination generate a resulting magnetic field, one or more properties of which can be varied by rotating the magnetic moments of the magnets about their respective rotation axis. Properties that can be varied include the orientation, the flux density as well as the spatial gradient of the resulting magnetic field.

In a further aspect of the invention, the problem is solved by a use according to claim 9. Any of the above magnetic field generators or the above methods is used for actuating a tethered device that possesses a magnetic moment. Alternatively, any of the above magnetic field generators or methods is used for actuating an untethered device that possesses a magnetic moment.

PREFERRED EMBODIMENTS OF THE INVENTION

Preferred features of the invention which may be applied alone or in combination are discussed in the following and in the dependent claims.

As explained above, a group of magnets has an orientation in the sense that each of the rotation axes of the magnetic moments of the magnets of the group is inclined by less than 15 degrees (provided that a full circle comprises 360 degrees) in relation to the group's orientation. In the following, if not otherwise stated, the term "group" always refers to a group with an orientation in the above sense. Preferably the rotation axis of the magnetic moment of each magnet of a group is inclined by less than 10 degrees, more preferably less than 5 degrees, more preferably less than 1 degree.

In a preferred embodiment of the invention, the magnetic field generator comprises at least one, more preferably two, more preferably three groups of magnets, the magnetic moment of each magnet being rotatable about a rotation axis, wherein each group comprises at least two magnets. In the case of two or three groups of magnets, the orientations of the groups are linearly independent. It is an achievable advantage of this embodiment of the invention, that a resulting magnetic field of arbitrary orientation and/or arbitrary flux density can be created. The preferred magnetic field generator does not comprise more than three groups.

Preferably, the orientation of each group forms with the orientation of each other group an angle of more than 50 degrees, more preferably more than 65 degrees, more preferably more than 70 degrees. In a particularly preferred embodiment of the invention the orientation of each group is "essentially perpendicular" to the orientation of each other group in the sense that the orientation of each group is perpendicular to the orientation of each other group with a deviation of less than 15 degrees. More preferably, the deviation is less than 10 degrees, more preferably less than 5 degrees, even more preferably less than 1 degree.

Preferably, one, more preferably two, more preferably three of the groups comprise more than two magnets, for example 3, 4, 5 or 6 magnets. This embodiment of the invention can exploit the fact that more magnets can provide for a more homogenous and/or a stronger resulting magnetic field or for a more homogenous or stronger gradient of the resulting magnetic field.

Preferably, the magnetic field generator comprises input means for a set of control parameters and the orientation and flux density of the resulting magnetic field is determined by the set of control parameters. More preferably, the set of control parameters comprises less than 6 control parameters, more preferably less than 5. In a particularly preferred embodiment of the invention, the number of control parameters is 3. This embodiment of the invention exploits the fact that three scalar parameters are sufficient to define an arbitrary orientation and magnetic moment of the resulting magnetic field of arbitrary orientation and/or arbitrary flux density. In another preferred embodiment of the invention, the number of control parameters is 2. This embodiment of the invention exploits the fact that two scalar parameters are sufficient to define any orientation in a two-dimensional space and an arbitrary flux density of the resulting magnetic field.

The preferred control parameters are independent in the sense that the value of each control parameter can be chosen independently of the value of the other control parameter(s). In a particularly preferred embodiment of the invention the relationship between the orientation and flux density of the resulting magnetic field on one hand and the control parameters on the other hand is a bijection.

In a preferred embodiment of the invention the control parameters determine the angles of rotation of the magnetic moments about their respective rotation axes. More preferably, each set of values of control parameters unambiguously determines the angles of rotation of the magnetic moments of the magnets. In a particularly preferred embodiment of the invention, for each group of magnets there is one control parameter that determines the angles of rotation of the magnetic moments of all magnets of the group and each group has a different control parameter. This embodiment of the invention exploits the fact that if the orientation and flux density of the resulting magnetic field is considered a vector, each group can contribute one component to this vector and the control parameter can control a combination of orientation and flux density of this component.

Preferably, the control parameters do not determine a translation of the magnets. Rather, the preferred control parameters determine only the angles of rotation of the magnetic moments of the magnets. Accordingly, in a preferred embodiment of the invention the magnets are not translatable but in fixed positions relatively to the work space. Thus, in a preferred magnetic field generator the angles of rotation of the magnetic moments determine the orientation and flux density of the resulting magnetic field.

The preferred magnets are permanent magnets. The permanent magnets are for example neodymium magnets that are made of an alloy of neodymium, iron and boron. Preferably, all magnets in the magnetic field generator have at least a coercive field strength of 600 kA/m. Preferably, all magnets of the same group, more preferably the magnets of all groups have the same strength. All magnets of the same group, more preferably all magnets of all groups are identical with a normal manufacturing accuracy.

The magnetic moment of at least one, preferably all magnets of a group are essentially perpendicular to the orientation of the rotation axis. In this context, "essentially perpendicular" means that the magnetic moments extent perpendicular to the orientation of the rotation axis with a deviation of less than 15 degrees. More preferably, the deviation is less than 10 degrees, more preferably less than 5 degrees, even more preferably less than 1 degree.

Preferably, at least one group of magnets has a "hub" in the sense that all magnets of this group have the same distance to the group's hub. More preferably, all groups each have a hub. Particularly preferably, the hubs of the various groups of the magnetic field generator coincide. Preferably, at least one group of magnets has a "plane" in the sense that all magnets of this group are arranged in this plane. More preferably, all groups each have a plane. Note that if a group has a hub and a plane, the magnets of this group are arranged in a circle. Preferably, all magnets of a group are arranged equidistantly in the sense that all magnets of the group have the same distance to the closest neighbouring magnet of the same group. Accordingly, in a particularly preferred embodiment of the invention all magnets of a group are arranged equidistantly on a circle.

Preferably, the magnetic moment of at least one magnet, preferably all magnets—in particular if the magnets are permanent magnets—is rotated by means of rotating the magnets about their respective rotational axis. The magnets preferably are driven by electrical motors. Yet, the invention also encompasses embodiments where the magnetic moment is rotated by other means. For example, the magnetic moment of an electric magnet that comprises several electric loops or coils can be varied by varying the electric currents supplied to individual loops or coils electric magnet.

In a preferred embodiment of the invention, in at least one group the magnets of the group are operationally coupled with regard to the rotation of the magnetic moments such that their magnetic moments rotate simultaneously by identical angles about their respective rotational axis. More preferably, in all groups the magnets of the respective groups are operationally coupled in this way. Preferably, the simultaneous movement of all operationally coupled magnets of a group is in the same direction (clockwise or counterclockwise). In other embodiments of the invention some magnets, for example half of the magnets, rotate in one direction while the other magnets, for example the other half, rotate in the opposite direction. In other words, the magnets are operationally coupled such that some magnet rotate clockwise while the other magnets rotate counter clockwise.

In a preferred embodiment of the invention in order to achieve the simultaneous movement of the magnetic moments, two or more magnets, most preferably all magnets of the group are connected to each other and/or to a motor via gearings, chains, belts or other mechanical transmits, for example cogwheel drive, a screw drive, a belt drive or a combination of these.

Preferably, at least one group has a "centre" in the sense that the angles of rotation of the magnetic moments about their respective rotation axis of any pair of magnets of the group are offset by value that is the product of a factor and the angular distance of the rotation axes of the two magnetic moments as measured from the groups centre. The factor preferably is two. The "angular distance" is an angle measured in a measuring plane in which the centre is located and which extends perpendicularly to the orientation of the group. The angular distance is the angle between the lines that extend from the centre to the intersections of the rotation axes of each magnetic moment of the pair of magnetic moments with the measuring plane. More preferably, all groups have a centre. Preferably at least one group, more preferably all groups have a hub and a centre, and even more preferably the two coincide. Preferably at least one group, more preferably all groups have a plane and a centre, and even more preferably the plane and the measuring plane coincide.

Preferably, in at least one group, more preferably in all groups, the magnets are located essentially on the edges of a parallelepiped, or essentially on intersecting circumferences on an ellipsoid. The preferred parallelepiped is a cuboid, particularly preferably it is a cube. The preferred ellipsoid is a spheroid, particularly preferably it is a sphere. The workspace preferably is located inside the parallelepiped or the ellipsoid. It is an achievable advantage of this embodiment of the invention that the workspace is accessible freely from six windows defined by the six faces of the parallelepiped or the six windows between the intersecting circumferences of the ellipsoid.

In the case of a parallelepiped, including a cuboid or a cube, the magnets preferably are located near the centre of the edges of the parallelepiped. In this context, "near the centre" means that the distance from centre of gravity of the magnet to the closer end of the edge is more than 70% of the distance from the centre of gravity of the magnet to the far right end of the edge. More preferably more than 80%, even more preferably 90%.

The skilled person will understand that the orientations, hubs, planes, centres, measuring planes, circles, edges and spheres discussed above in typical embodiments of the invention are imaginary and not physically embodied. Nevertheless, the invention also includes embodiments in which one or more of these find physical equivalents, for example in the form of shafts, beams, panels and holes for purposes of construction.

The maximum achievable flux density of the resulting magnetic field generated in a work space by the magnets in combination in each one of the achievable orientations of the resulting magnetic field is larger than 90 gauss. As already defined further above, the "flux density of the resulting magnetic field" in the workspace is the arithmetic mean of flux density of the resulting magnetic field in the workspace. Preferably, the flux density of the resulting magnetic field in the workspace is "homogenous" in the sense that there is no point in the workspace that magnetic flux density of which deviates by more than 20%, preferably more than 10%, more preferably more than 5% from the flux density of the resulting magnetic field in the workspace (ie the arithmetic average flux density in the workspace). Preferably, the orientation of the resulting magnetic field in the workspace his homogenous in the sense that there is no point in the workspace that magnetic field orientation of which deviates by more than 10%, preferably more than 5% from the orientation of the resulting magnetic field in the workspace (ie the arithmetic average orientation in the workspace). Preferably the workspace has a volume of more than 1 cm$^3$ (cubic centimetre). Preferably, the direction of the resulting magnetic field can be changed at a speed larger than 0.1 degrees per second, more preferably larger than 1 degree per second.

In a preferred embodiment of the invention, the workspace by means of rotating the magnetic moment of one or more of the magnets a spatial gradient of the flux density of the resulting magnetic field generated in the workspace by the magnets in combination can be changed. Preferably, the orientation and flux density of the resulting magnetic field is determined by the set of control parameters. Preferably, the direction of the spatial gradient can be changed at a speed larger than 0.1 degrees per second, more preferably larger than 1 degree per second.

The magnetic field generators or the above methods preferably are used for actuating a tethered device that possesses a magnetic moment. Alternatively, any of the above magnetic field generators or methods is used for actuating an untethered device that possesses a magnetic moment. "Untethered" means that the medical device is not physically (ie material) connected to the outside of the workspace; whereas "tethered" refers to a device tools that has a physical (ie material) connection to the outside of the workspace.

Preferably, the magnetic field generator or the method is used to actuate and steer a miniaturized device in biological tissues or organs or lumens or inside an animal or inside a human body. In particularly preferred embodiments of the invention, the magnetic field generator us used to actuate and steer a miniaturized propeller, a stent, an implant, a particle, a magnet, an actuator, an end-effector, a robot, a gripper, a lens, a needle, a tubing, an endoscope, a catheter, an optical fibre, an electric wire or a medical device.

BRIEF DESCRIPTION OF THE DRAWINGS

In the following, further preferred embodiments of invention are illustrated by means of examples. The invention is not limited to these examples, however.

The drawings schematically show.

DETAILED DESCRIPTION OF AN EMBODIMENT OF THE INVENTION

Figure 1:
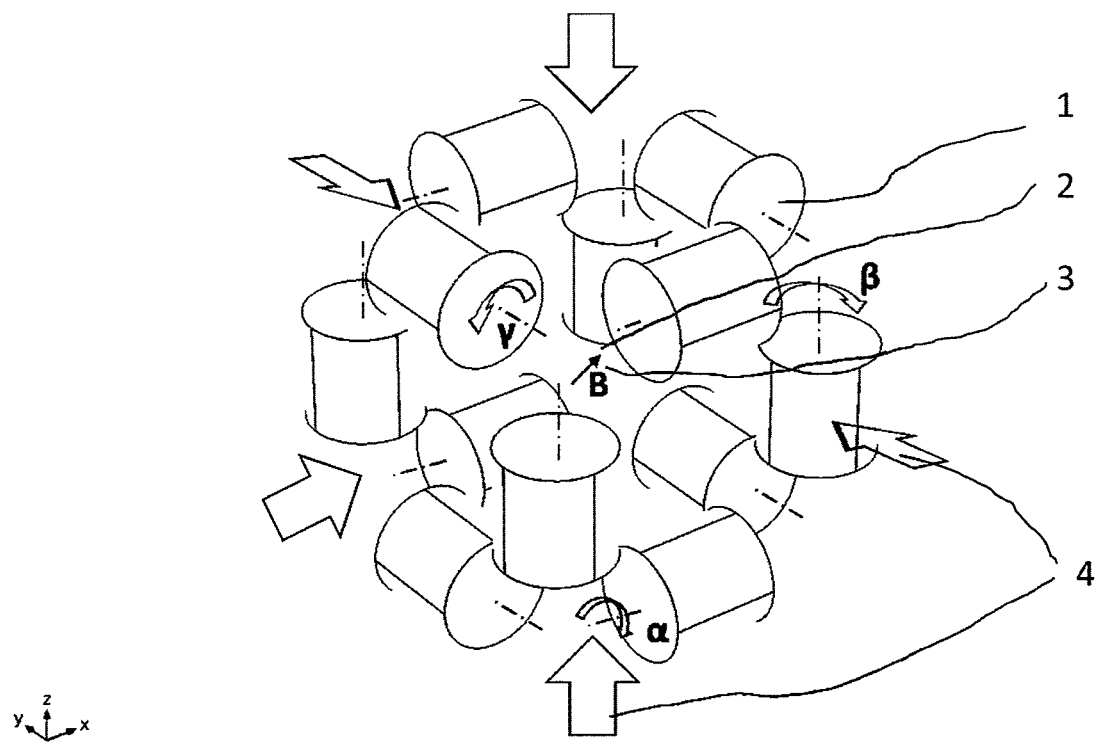
FIG. 1 A schematic perspective view on a magnetic field generator with cylindrical magnets.

In the following description of preferred embodiments of the invention, identical reference numerals refer to identical or similar components.

Example: Magnetic Field Generator with 12 Magnets

Figure 2:
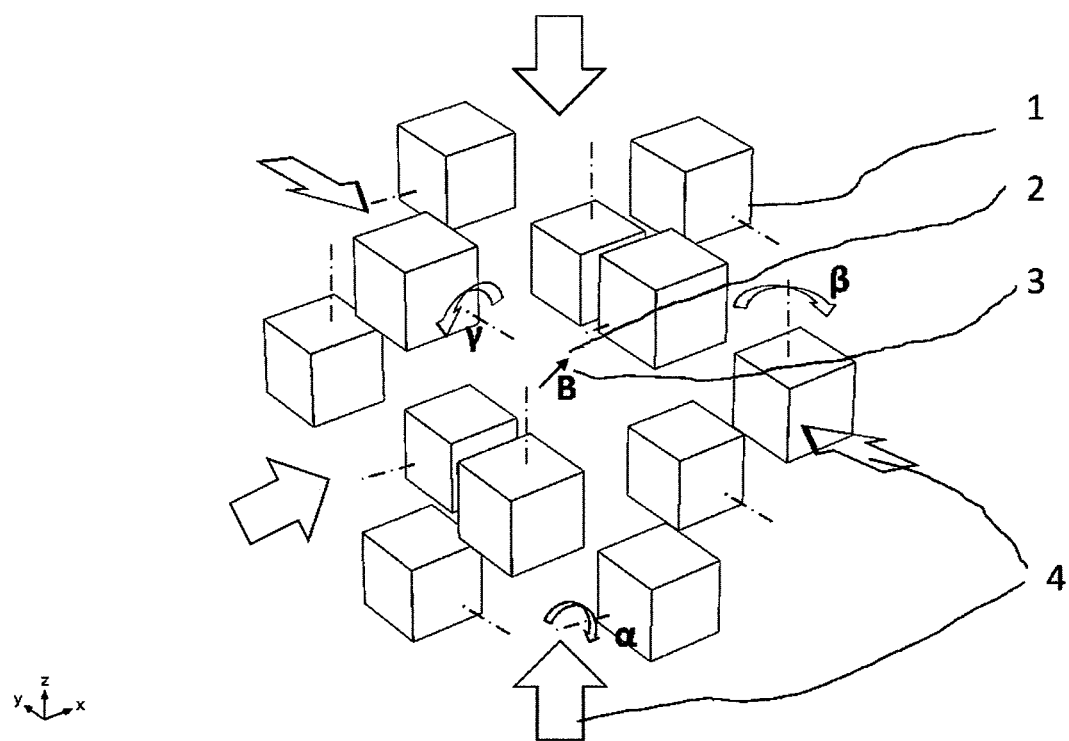
FIG. 2 A schematic perspective view on a magnetic field generator with cubic magnets.
Figure 3:
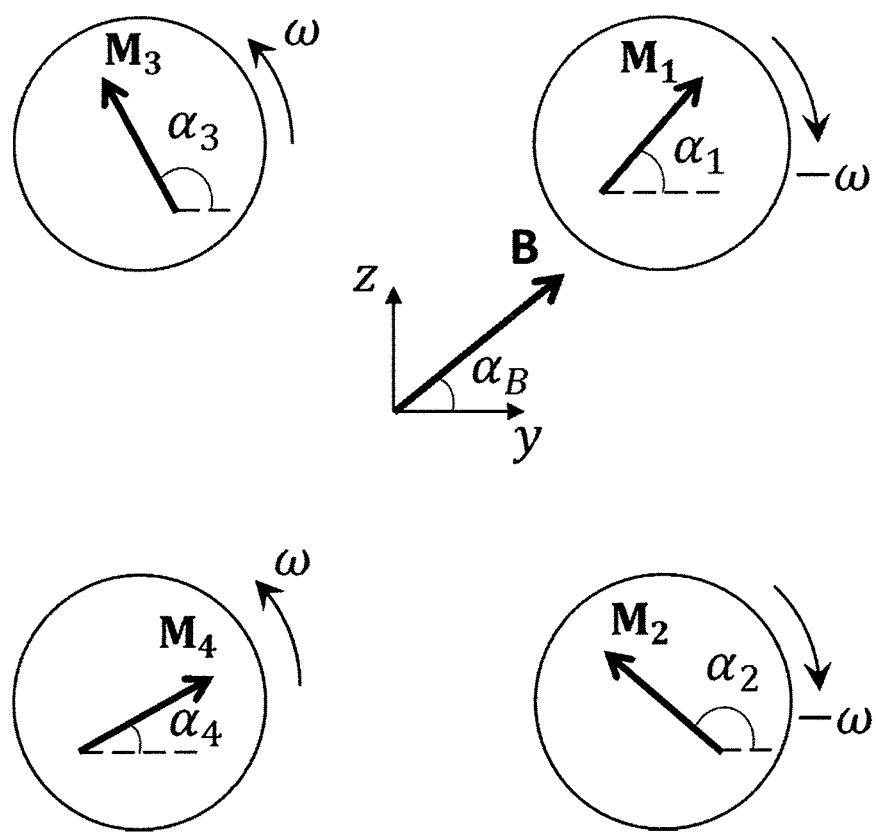
FIG. 3 A cross-sectional view through one group of the permanent magnets in the magnetic field generator in FIG. 1; their magnetic moments $M_1$, $M_2$, $M_3$ and $M_4$ are of the same magnitude within manufacturing errors and all magnetic moments extend in the paper plane. Yet, they have different rotation angles $\alpha_1$, $\alpha_2$, $\alpha_3$, $\alpha_4$ about their rotation axes, which extend perpendicularly to the paper plane. Moreover, all magnetic moments rotate at the same absolute value of angular velocity $|\omega|$ but two magnetic moments rotate clockwise while the other two rotate counter-clockwise.

The magnetic field generator illustrated in FIGS. 1 to 3 comprises of three groups of permanent magnets 1, and four parallel magnets 1 belong to each group. Each magnet 1 in the drawing is in a cylindrical or cubical shape, yet other shapes would also be possible, for example spherical or cuboid shapes. The permanent magnets 1 have closely matched magnetization and strength and a permanent magnetization direction. They are arranged to be rotated by electrical motors (not shown) around an axis that is perpendicular to the magnets 1 magnetic moment $M_i$. Combined, the magnets generate resulting a magnetic field 2 with field vector B at the centre of the magnetic field generator where the workspace 3 is located.

For many applications, it is beneficial to generate a homogeneous magnetic field 2 in a large workspace 3 with negligible magnetic gradient force. In the magnetic field generator of figured 1 to 3, the magnets 1 are arranged equidistantly to their next neighbours and in a circle around a hub that is located in centre of the workspace 3, so as to minimize spatial and temporal gradients of the resulting magnetic field 2. Should the magnets 1 differ in their magnetization, then in principle it is possible to compensate differences in the physical properties by an arrangement of the magnets 1 where these no all longer have the same distance from the hub or are no longer arranged equidistantly from their next neighbours.

Advantageously, in the arrangement of FIGS. 1 to 3, only three independent angular inputs (labeled as α, β, γ in FIGS. 1 and 2), are needed to change the direction of the field vector B to point in an arbitrary direction in three-dimensional space while also allowing for the adjustment of the B field flux density. The flux density can be zero, but not larger than a maximum achievable flux density specific to the respective orientation of the vector B. Although there are in total 12 magnets (3 groups times 4 magnets per group) in the magnetic field generator shown in FIGS. 1 to 3, only three independent rotational inputs are required, thus only three motors are needed for the setup.

In each group, there are at least 2 magnets (arranged on opposing sides of the workspace); and there can be more than four magnets 1, as more magnets 1 result in a higher flux density over a larger workspace 3. The mechanical driving mechanism (not shown) of the magnets 1 does not require the direct connection to a particular magnet 1, and can include a belt drive, a gear driven or other means of actuation.

Figure 4:
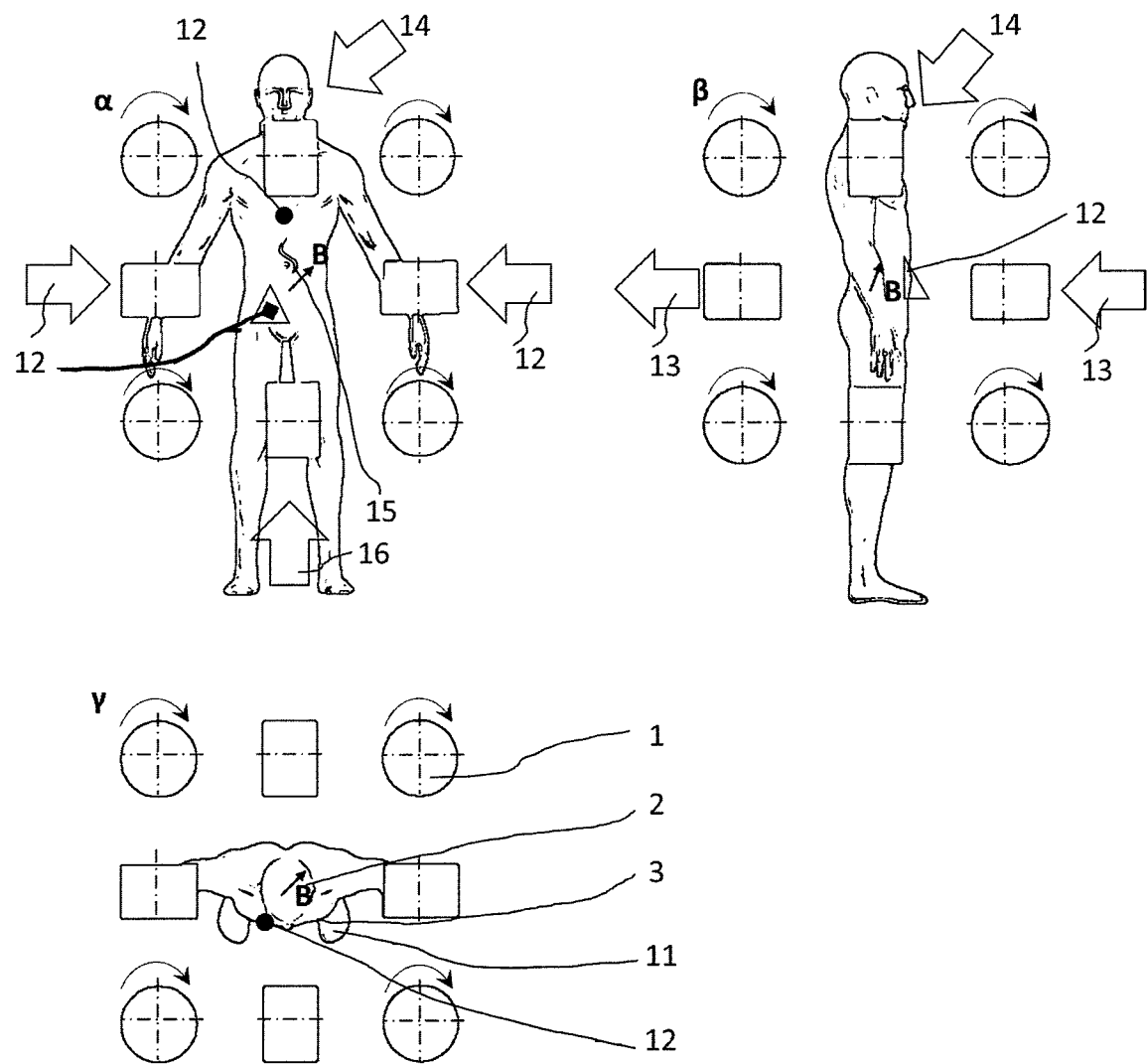
FIG. 4 A schematic representation of a magnetic field generator with three groups of magnets actuating a untethered medical device inside the human body; the view on the left side of the top row is a top view, the view on the right side of the top row is a side view, and the view on the bottom is a front view.
Figure 5:
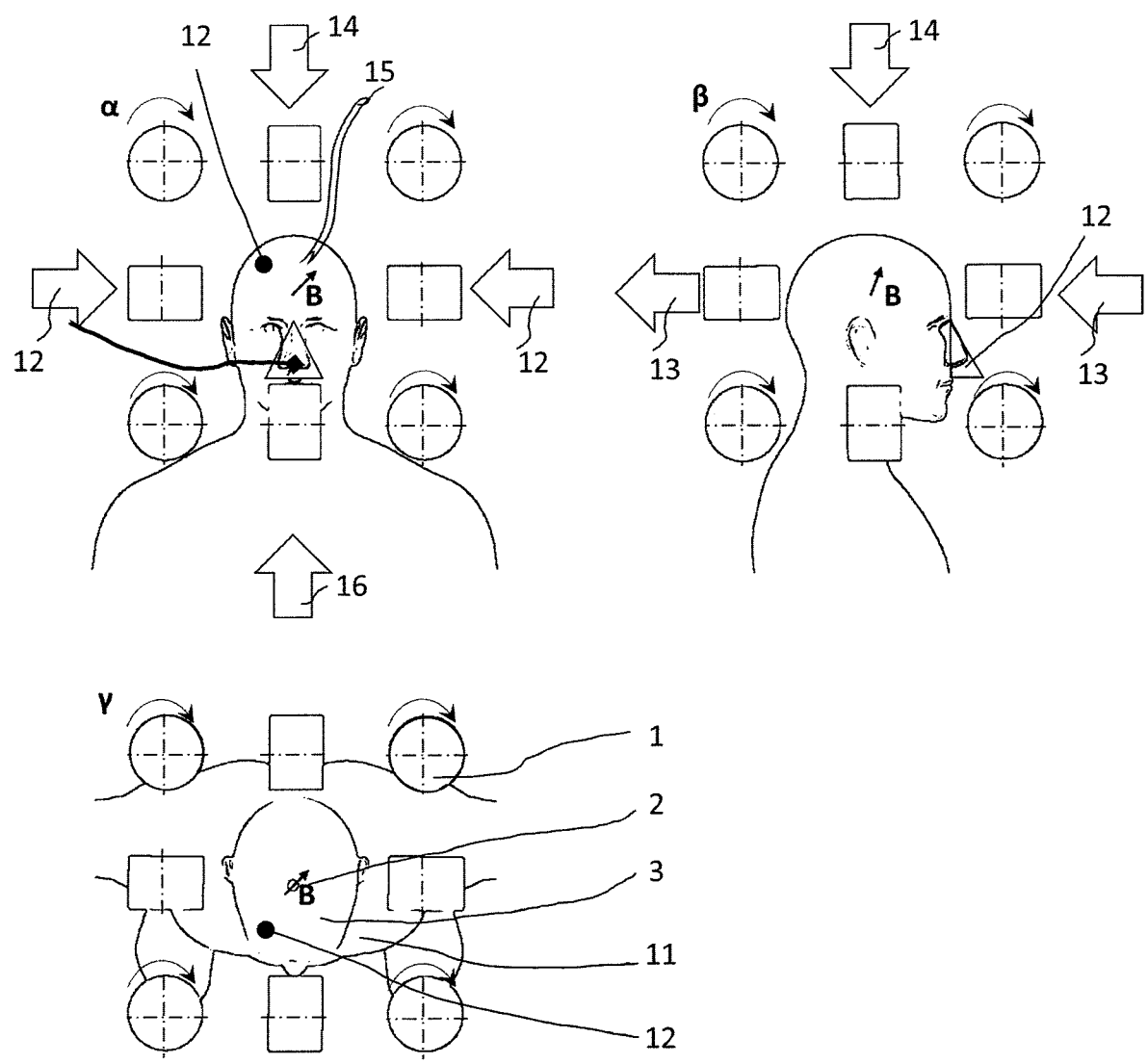
FIG. 5 A schematic representation of a magnetic field generator with three groups of magnets actuating a tethered medical device inside the human body; the view on the left side of the top row is a top view, the view on the right side of the top row is a side view, and the view on the bottom is a front view.

As the magnets 1 are placed on the edges of a cube, the workspace 3 can be accessed from many directions. Only one rotational degree of freedom is required for each magnet 1, and there is no translational motion of the magnets 1. This design feature allows changes of the magnetic field 2 to be realized; and it also enables long-term accessibility to the workspace 2. Shown as hollow big arrows in FIGS. 1 and 2, the workspace 3 can be accessed from the four sides between the magnets 1, and also from the top and bottom. This is beneficial, for example in the clinical application as shown in FIGS. 4 and 5. A patient 11 can lie on a bed sliding into the magnetic field generator via patient access 16; and anaesthetic tubes, intravenous (IV) injections and electrical sensors 12 can stay connected to the patient 11 during the operation. Moreover, medical imaging modalities (x-ray, computer tomography (CT), ultrasound, optical, etc) are also allowed from the top or side imaging access 13.

Possible applications of the invention include but are not limited to: (1) driving a propeller or robot to swim or drill through biological fluids or tissues as for example disclosed in the European Patent Applications 17 166 356 and 17 187 924; (2) steering an optical fibre or an electric wire to cut through biological tissues; (3) steering an endoscope or catheter in a body lumen; (3) driving a wireless miniaturized actuator; (4) driving magnetic micro- or nano-particles under the microscope, for biological study or for delivery, eg into a cell, or for a microrheology study; and (5) magnetically steering an electron beams.

Example: Actuation of a Medical Device in a Human Body

An exemplary application of the disclosed invention is to actuate and steer and control a medical device inside the human body by the generated magnetic field. Two embodiments are shown in FIG. 4 and FIG. 5, to actuate an untethered medical device and a tethered medical instrument respectively. A tethered medical device has a physical material connection leading to the outside of the workspace, such as cable; an untethered medical device does not have such connection.

In FIG. 4, an untethered medical device 15 is actuated by the magnetic field 2 in the workspace 3. As the device 15 has a finite magnetic moment (eg due to a permanent magnet is attached to the device), it tends to align with the external magnetic field 2 direction. The magnetic field 2 from the magnetic field generator can be used to exert a torque on the medical device 15 and is actuated in this way. The device 15 can have a suitable shape, eg that of a helical propeller, to enable its translational motion during rotation. The device 15 can have multiple segments that have multiple magnetic moments so that the shape of the device is changed under the actuation of the magnetic field 2. For example, the medical device can be a gripper or a stent that opens and closes, a valve that opens and closes, or a pump that moves periodically.

In FIG. 5, a tethered flexible medical instrument 15 is steered by the magnetic field 2 in the workspace 3. A part of the patient's 11 body (in the example of FIG. 5 the head, for neurosurgery) is placed in the magnetic field generator through one of the open spaces defined as access 16. A surgical tool 15, for instance, can be applied through the workspace via another access 14. As the tip of the tool 15 is equipped with a permanent magnetic moment, which here is assumed to point along the long axis of the instrument 15 (eg due to a permanent magnet encapsulated at the tip), the tip can be made to align with the external magnetic field 2 direction and the orientation of the instrument 15 tip is controlled in this way. Alternately, the flexible instrument 15 steered with the disclosed method can be an endoscope, a catheter, an optical fibre, a bundle of optical fibres, a tube, a wire, a gripper or any other suitable instrument.

The invention can be used to steer an active device to cut through biological tissues, eg an optical fibre that transmits laser light (for example pulsed laser light) to cut through biological tissue.

The part of the human or animal body placed in the magnetic field generator can be a head, brain, eye, arm, leg, knee, hand, foot, or any other desired part of the body (whole or in part). The position of the patient 11 relative to the magnetic field generator can be adjusted. The monitoring of the device or instrument 15 in the human body is accomplished by a suitable medical imaging modality. The positional information of the device or the tip of the instrument 15 is can be used as an input signal in a feedback control loop to drive the field generator, and the relative position of the patient 11 and the field generator can be adjusted to keep the device 15 or the tip of the instrument 15 well inside the workspace 3, for example near its centre. In another case, the workspace 3 of the field generator is larger than the required movement range of the device 15, so the position of the patient 11 is fixed relative to the field generator.

The device or instrument 15 can be actuated or steered in solid or liquid biological tissue, eg brain, liver, prostate, muscle, skin, eye or in an organ, or in a body lumen, such as urinary tract, kidney, urinary bladder, eye, heart, stomach, lung, blood vessel, or any other suitable biological tissue.

The device may also be steered by means of the magnetic field generator or the method according to the invention while an additional external force is provided to a tethered medical device. In this embodiment the magnetic field generator provides the direction control while the force required to penetrate tissue or other biological material is provided by other means.

There are several advantages of the magnetic field generator and the method according to the invention: a) it is a potentially wireless approach, thus it allows more dexterity of the medical device 15; b) the workspace 3 is large enough to incorporate the human body or a part of the human body; c) a high magnetic flux density is realized, thus it results in larger actuation force or torque on the device 15; and d) the accesses 16 to the workspace 3 allows the positioning of the patient 11, the connection and inclusion of other medical instruments, e.g. IV tubes 12, anesthesia tubes 12, sensors 12, and the application of medical imaging instrument 13 and surgical tools 14, eg scalpel, scissors, needle.

Analytical Theory for Generating a Superimposed Magnetic Field

With the invention, it is possible to generate a controlled magnetic field 2 in both the field strength and the direction in the workspace 3. In order to explain the theory behind the invention, first a situation is discussed in which one group of magnets 1 creates resulting magnetic field 2 with a fixed strength and continuously changing direction. Then, a situation is explained where one group of magnets 1 creates a resulting magnetic field 2 of fixed direction with oscillating strength. Finally, a resulting magnetic field 2 with arbitrary orientation and flux density is discussed.

Spatially Homogeneous Resulting Field that Rotates

Four magnets 1 in one group are shown as an example in this embodiment to control the in-plane resulting magnetic field 2. The magnets 1 have the same magnitude of their magnetic moment, and they are distributed equidistantly from their next neighbours and at identical distances from hub of the group. A spatially homogenous field 2 in the workspace that rotates around the x axis is described by the following equations:

$$B_y = B_0 \cos \alpha_B \quad (1.1)$$

$$B_z = B_0 \sin \alpha_B \quad (1.2)$$

where $B_y$ and $B_z$ are the component of the magnetic field 2 in y and z direction, respectively, and $\alpha_B$ is the angle between the magnetic field 2 and the y axis as illustrated in FIG. 3.

Each permanent magnet 1 is a cylindrical or disk-shaped magnet 1 that has a magnetic dipole in the diametric direction, and rotates around its cylindrical axis (which is along x, and which is perpendicular to the dipole moment), as shown in FIG. 3. The magnetization vectors $M_i$ are oriented by an angle $\alpha_i$ in the yz-plane. The magnetic field 2 vector B resulting from the superposition of the magnetic fields generated by the four dipoles at point p is given by:

$$B(p) = \sum_{i=1}^{4} \frac{\mu_0 |M_i|}{4\pi |r_i|^3} (3\hat{r}_i \hat{r}_i^T - I) \hat{M}_i \quad (2)$$

where $\mu_0 = 4\pi \times 10^{-7}$ T·m·A$^{-1}$ is the permeability of free space, I is the 3×3 identity matrix, $r_i$ is the vector from the magnet 1 i to point p, $\hat{r}_i$ is the unity vector in the direction of $r_i$. A maximum combined field strength (ie flux density) in the yz-plane at the hub of the group is found for the orientation:

$$\alpha_1 = \alpha_4 = \alpha_0 \quad (3)$$

$$\alpha_2 = \alpha_3 = \alpha_0 + \pi \quad (4)$$

where $\alpha_0$ is defined as shown in FIG. 3 and is the initial angle for the magnets 2 according to the initial angle of the magnet field $\alpha_{B0}$:

$$\alpha_0 = \frac{\pi}{2} - \alpha_{B0} \quad (5)$$

It follows that when the magnetic moments of the magnets 1 are aligned pairwise in the diagonal position, ie the pairs $M_1$ & $M_4$, and $M_2$ & $M_3$, respectively, but they are opposed to each other (180° phase difference) between the two pairs, then a maximum resulting field strength is obtained. This state is taken to be the initial state, and from this state, the magnets 1 are mechanically rotated with the same angular velocity clockwise $\alpha_B = \alpha_{B0} - \omega t$, so that their magnetic fields rotate with the same angular velocity $\omega$ but counter-clockwise, and the rotation angle is $\varphi = \omega t$:

$$\alpha_1 = \alpha_0 + \varphi \quad (6)$$

$$\alpha_2 = \alpha_0 + \pi + \varphi \quad (7)$$

$$\alpha_3 = \alpha_0 + \pi + \varphi \quad (8)$$

$$\alpha_4 = \alpha_0 + \varphi \quad (9)$$

Figure 6:
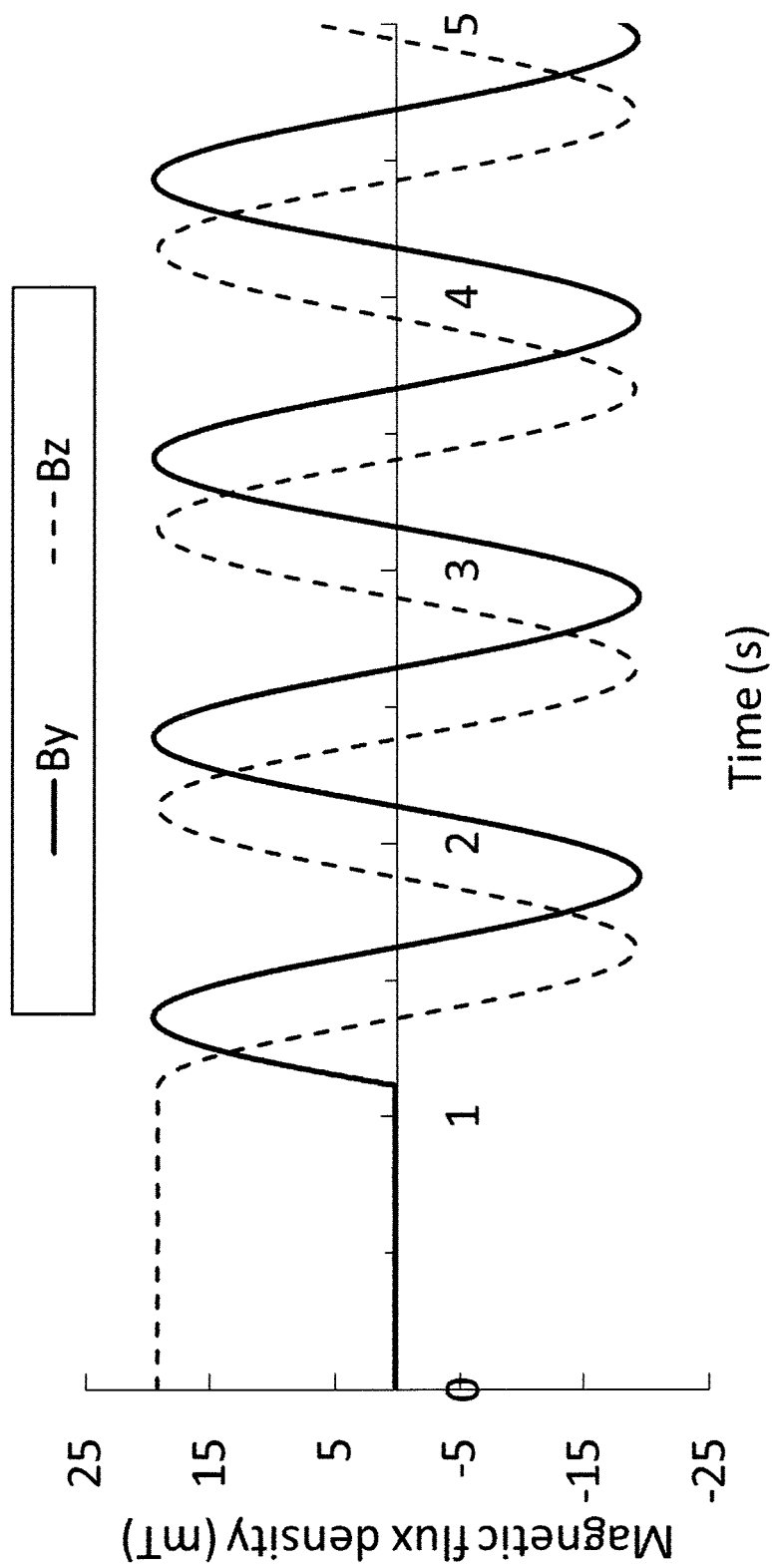
FIG. 6 The components of a resulting magnetic field as generated by a group of four rotating magnets and measured in the workspace; the magnets are spherical with a diameter of 30 mm and a coercive field strength of approximately 955 kA/m. The resulting magnetic field is a spatially homogeneous field of 20 mT that rotates at 1 Hz starting at about 1 s.
Figure 7:
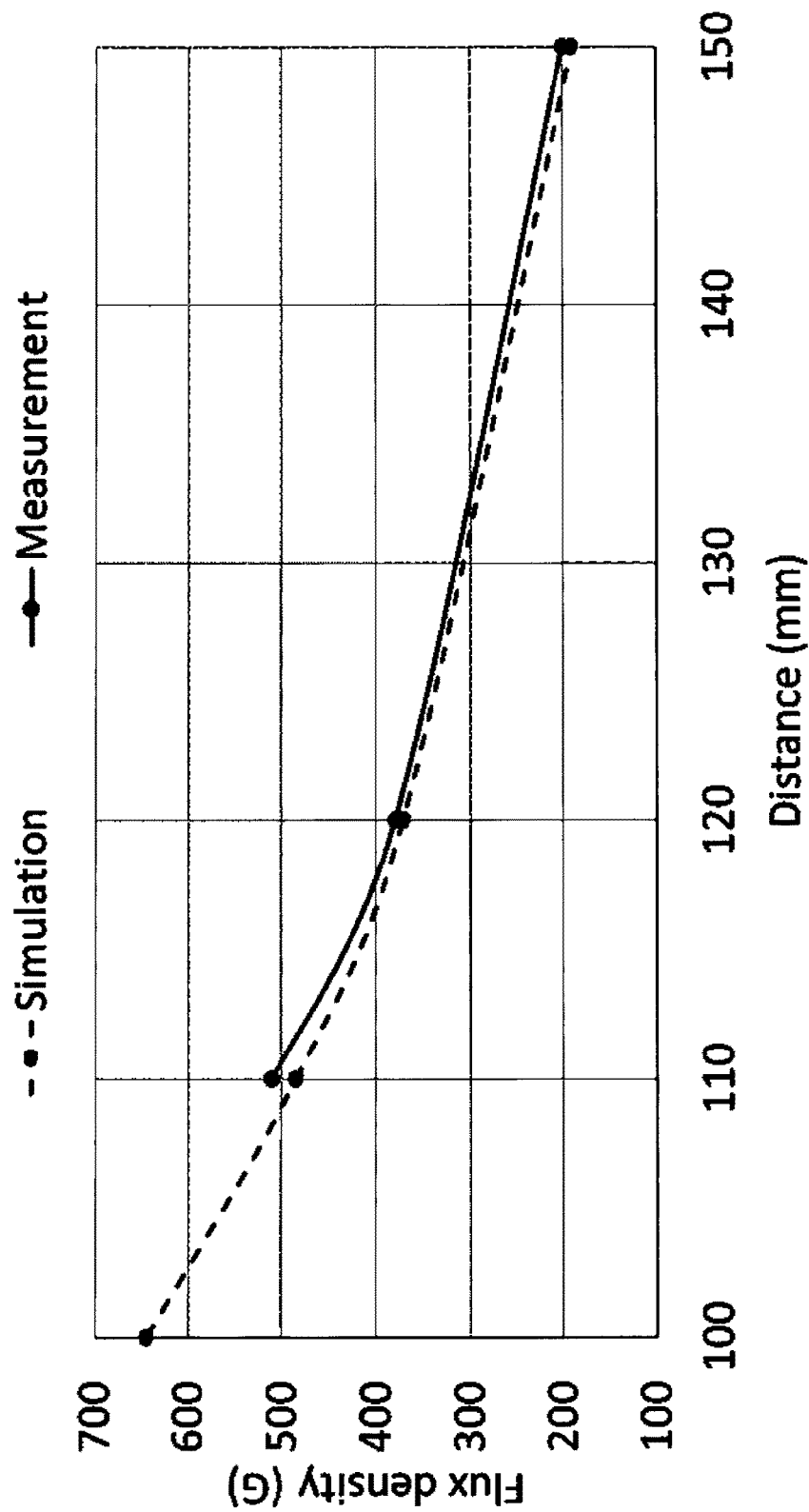
FIG. 7 The results of measurements of the maximum magnetic field generated by a group of magnets compared with the results of a simulation.

The measured resulting magnetic field 2 follows the theoretical prediction. As shown in FIG. 6, the components in the y and the z directions oscillate with a phase difference of $\pi/2$, thus the combined field is constant in strength and rotates around the x axis. The maximal field $B_{max}$ that can be achieved by the set-up, where the coercive field strength of each spherical magnet with a diameter of 30 mm is approximately 955 kA/m, is also measured as a function of the distance between the magnets, as shown in FIG. 7. The measurement fits the simulation very well, and the maximal strength for the current set-up exceeds 500 G in the current set-up.

Oscillating Resulting Field Along a Given Axis

The oscillating resulting magnetic field 2 has a fixed oscillation axis (direction) defined as $\alpha_B$, which is the angle to the y axis, and a field strength oscillates, which is given by:

$$|B| = B_{max} \cos \varphi \quad (10)$$

where $B_{max}$ is the maximal field strength (ie flux density) that could be achieved by the superposition of the four magnetic dipoles, and $\varphi=\omega t$ is the oscillating angle, and w is the angular velocity.

The geometry of the set-up and the initial conditions are the same as in Equations (3)-(5). The difference is that two pairs of magnets 1 rotate in opposite directions. Specifically, as illustrated in FIG. 3, $M_1$ and $M_2$ rotate clockwise with an angular velocity of $-\omega$, and $M_3$ and $M_4$ rotate counterclockwise with an angular velocity of $\omega$. The oscillating angle is $\varphi=\omega t$, so the rotational angles of the four magnets 1 are given by:

$$\alpha_1=\alpha_0-\varphi \qquad (11)$$

$$\alpha_2=\alpha_0+\pi-\varphi \qquad (12)$$

$$\alpha_3=\alpha_0+\pi+\varphi \qquad (13)$$

$$\alpha_4=\alpha_0+\varphi \qquad (14)$$

With this approach, two outputs, ie the magnitude and the direction of the resulting magnetic field 2 at the hub of the group of magnets 1, are fully controlled with two independent inputs $\alpha_0$ and $\varphi$.

Figure 8:
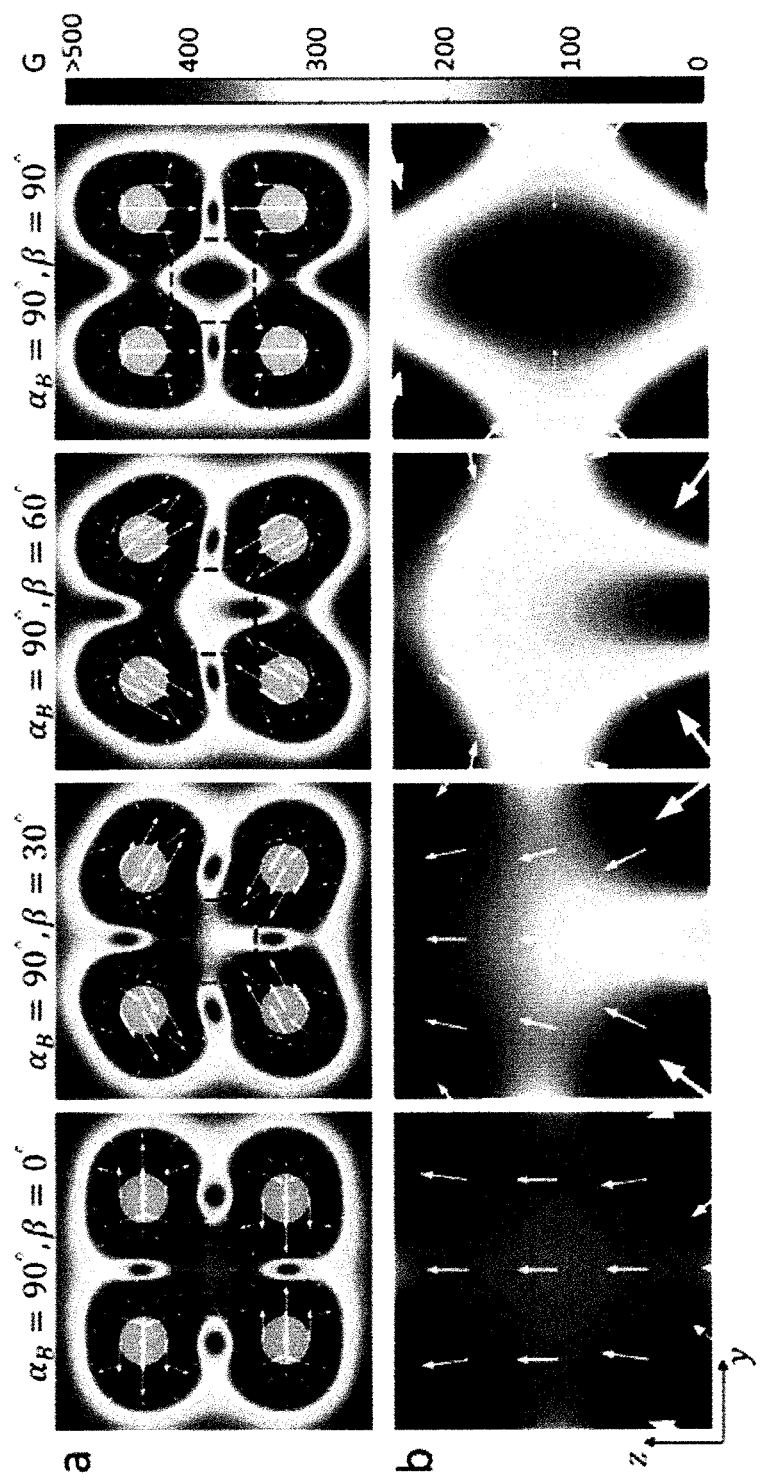
FIG. 8 The results of a simulation of a resulting magnetic field that oscillates along the z axis.
Figure 9:
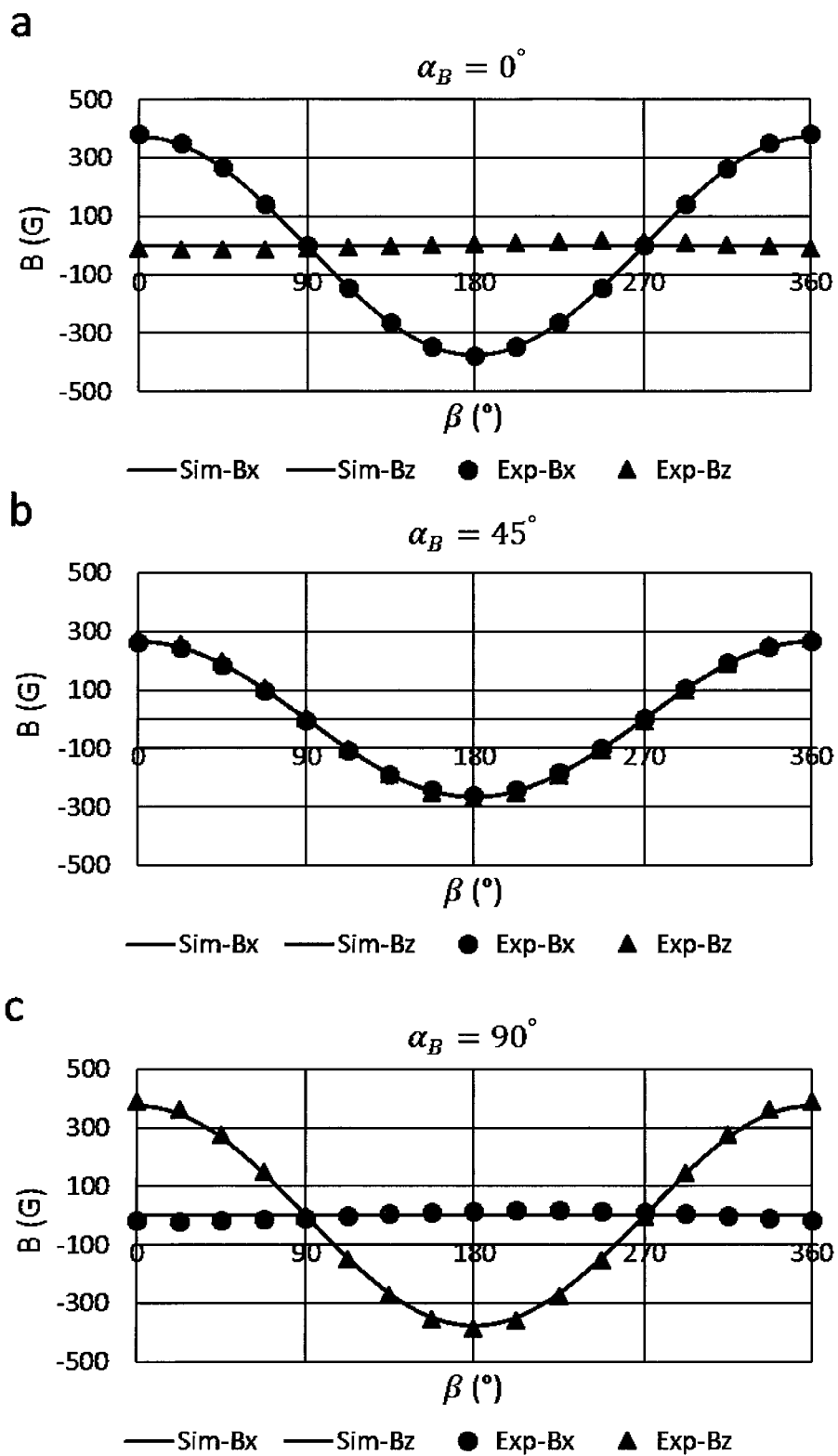
FIG. 9 The results of a simulation ("Sim") and of measurements ("Exp") of an oscillating resulting magnetic field B (G) with three different orientations within the x-y-plane: (a) $\alpha_B=0°$. (b) $\alpha_B=45°$. (c) $\alpha_B=90°$. The fields' components in x and z direction are labelled as "$B_x$" and "$B_z$", respectively; the curves are results from simulations (labeled as "Sim") and the markers are experimental results (labeled as "Exp")

The simulation results of the magnetic flux density are shown in FIG. 8. In this embodiment, a resulting magnetic field 2 oscillating in the z direction ($\alpha_B=90°$) is shown as an example. Simulations also show that the resulting magnetic field 2 increases non-linearly from a maximum of about 374 G at a distance of 120 mm, to a maximum of about 485 G at a distance of 110 mm, to a maximum of about 645 G at 100 mm. This is achieved with the same magnets 2, all having a relatively small diameter of 30 mm. It clearly demonstrates the advantage of the permanent magnet 1 set-up over electromagnetic ones, as the field can easily achieve 3 to 6 times the strength of a common electromagnet, without any special cooling requirement or the need for expensive power amplifier systems. The resulting magnetic field 2 at the hub was measured by a gaussmeter and plotted in FIG. 9. The experimental results fit the simulations very well.

Resulting Field with Arbitrary Orientation and Flux Density

The magnetic field generator disclosed here can also generate a magnetic field 2 vector B pointing in any arbitrary direction within the three-dimensional space enclosed by the magnets 1 and the magnitude of the resulting magnetic field 2 can also be controlled. It is The direction and the strength of the resulting magnetic field is fully controlled with only three independent angular control parameters for each group of magnets (labelled as $\alpha$, $\beta$, $\gamma$ in FIGS. 1 and 2); at the same time, the flux density of the generated B field is tuned in the range from zero to the maximal achievable flux density.

Figure 10:
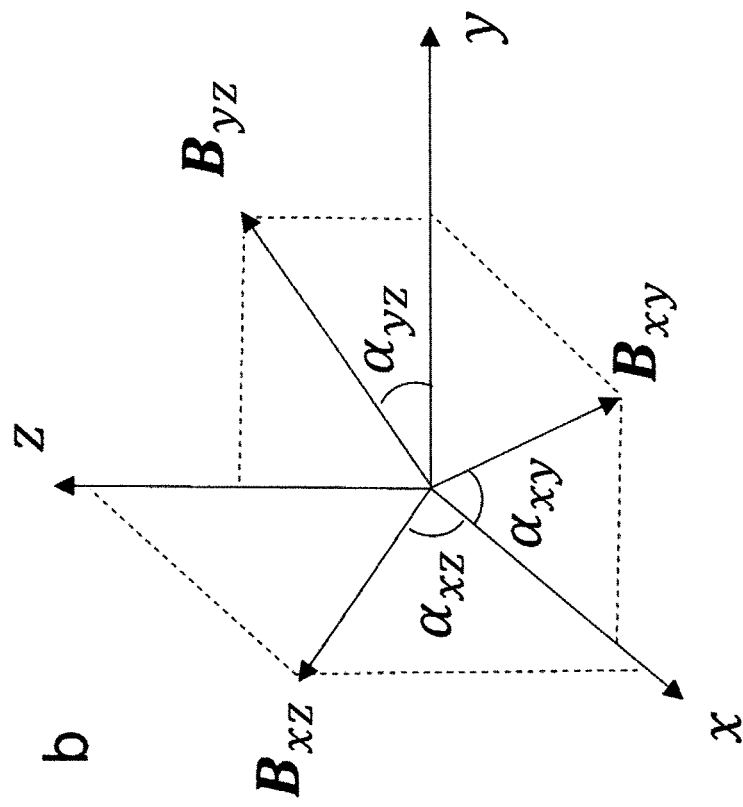
FIG. 10 (a) a schematic drawing identifying the component vectors $B_x$, $B_y$ and $B_z$, of a resulting magnetic field B along the axes of a coordinate system and angles defining the orientation of the magnetic field vector in the coordinate system; and (b) a schematic drawing of the three magnetic fields $B_y$, $B_{xz}$ and $B_{yz}$, each generated by the magnetic moments of a different one of three groups of magnets; the orientation of the latter three magnetic fields is defined by the angles $\alpha_{xy}$, $\alpha_{xz}$, and $\alpha_{yz}$, respectively.
Figure 10:
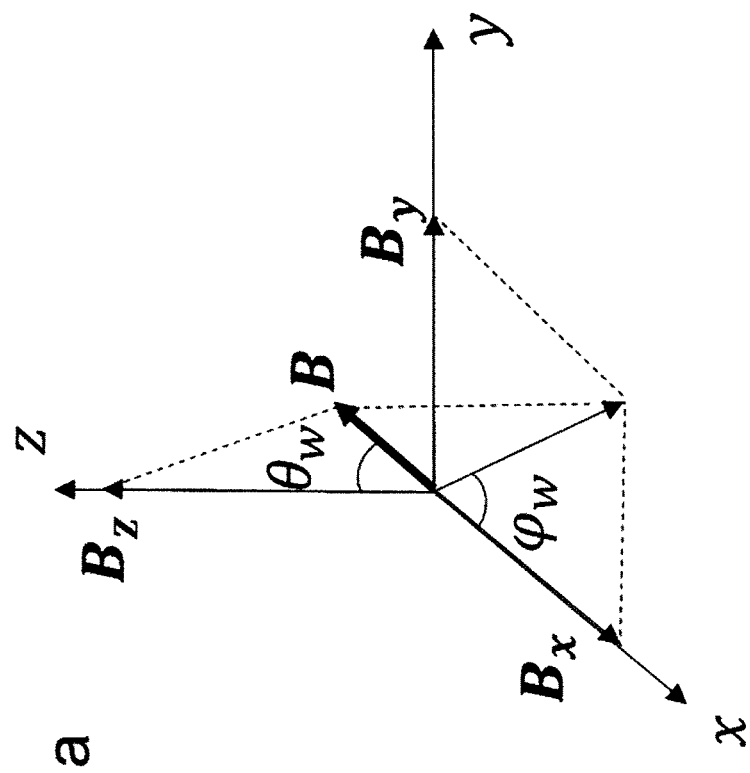

The desired resulting magnetic field 2 in the workspace is:

$$B=B_0\hat{w}=[B_x,B_y,B_z]^T=B_0[\sin\theta_w\cos\varphi_w, \sin\theta_w\sin\varphi_w, \cos\varphi_w]^T \qquad (15)$$

where $\hat{w}$ is the unity vector in the direction of B, $B_0$ is the field strength (ie the flux density), and $\theta_w$, $\varphi_w$ are the angles between the vector and the axes, as shown in FIG. 10a. $[\bullet]^T$ is the transpose symbol.

The resulting magnetic field 2 is the sum of three magnetic vectors generated by each group of magnets 1 that are orthogonal to each other, thus:

$$B=B_{xz}+B_{yz}+B_{xy} \qquad (16)$$

where $B_{xz}$, $B_{xz}$, $B_{xy}$ are the in-plane magnetic field vector generated by each group of permanent magnets 1. As in FIG. 10b, the composed magnetic field B can be written in three components form:

$$B=[B_x,B_y,B_z]^T=[B_{xy}\cos\alpha_{xy}+B_{xz}\cos\alpha_{xz},B_{yz}\cos\alpha_{yz}+B_{xy}\sin\alpha_{xy},B_{xz}\sin\alpha_{xz}+B_{yz}\sin\alpha_{yz}]^T \qquad (17)$$

where $B_{xy}$, $B_{xz}$, $B_{yz}$ are the field strengths generated by only one group of magnets 1 in the xy-, xz- and yz-planes, respectively, and $\alpha$ . . . are the angles between the in-plane vector and the axes, as shown in FIG. 10b.

In some embodiments, magnets 1 with the same size, the same magnetic moment and the same distances from the hub of their group are used, then the field strength in each directions are equal and the equation (16) is simplified with $B_{xy}=B_{xz}=B_{yz}=B_1$. Equating equations (15) and (17) results in the following equation:

$$B_1\begin{bmatrix}\cos\alpha_{xy}+\cos\alpha_{xz}\\ \cos\alpha_{yz}+\sin\alpha_{xy}\\ \sin\alpha_{xz}+\sin\alpha_{yz}\end{bmatrix}=B_0\begin{bmatrix}\sin\theta_w\cos\varphi_w\\ \sin\theta_w\sin\varphi_w\\ \cos\varphi_w\end{bmatrix} \qquad (18)$$

The right side of equation (17) defined the required composed magnetic field with three parameters $B_0$, $\theta_w$, $\varphi_w$, and solving equation (18) will lead to the three unknown parameters $\alpha_{xy}$, $\alpha_{xz}$, $\alpha_{yz}$ on the left side of the equation. From the instrument controlling point of view, three input parameters of the angles in each direction $\alpha_{xy}$, $\alpha_{xz}$, $\alpha_{yz}$ results in full control of three output parameters $B_0$, $\theta_w$, $\varphi_w$, which are the magnitude and the three-dimensional direction of the magnetic field vector. In some embodiments, the equation (18) is solved numerically in Matlab (R2017a, MathWorks).

In some embodiments, the groups of magnets are not orthogonal to each other, but the equation (16) is still valid. Decomposition of each magnetic field vector into the three axes will result in a new set of equations (17) and (18), but the general principle is the same as demonstrated herein, ie by controlling three input parameters of the angles $\alpha$ . . . in three different directions results in the full control of three output parameters $B_0$, $\theta_w$, $\varphi_w$, which are the magnitude and the 3D direction of the magnetic field vector.

Figure 11:
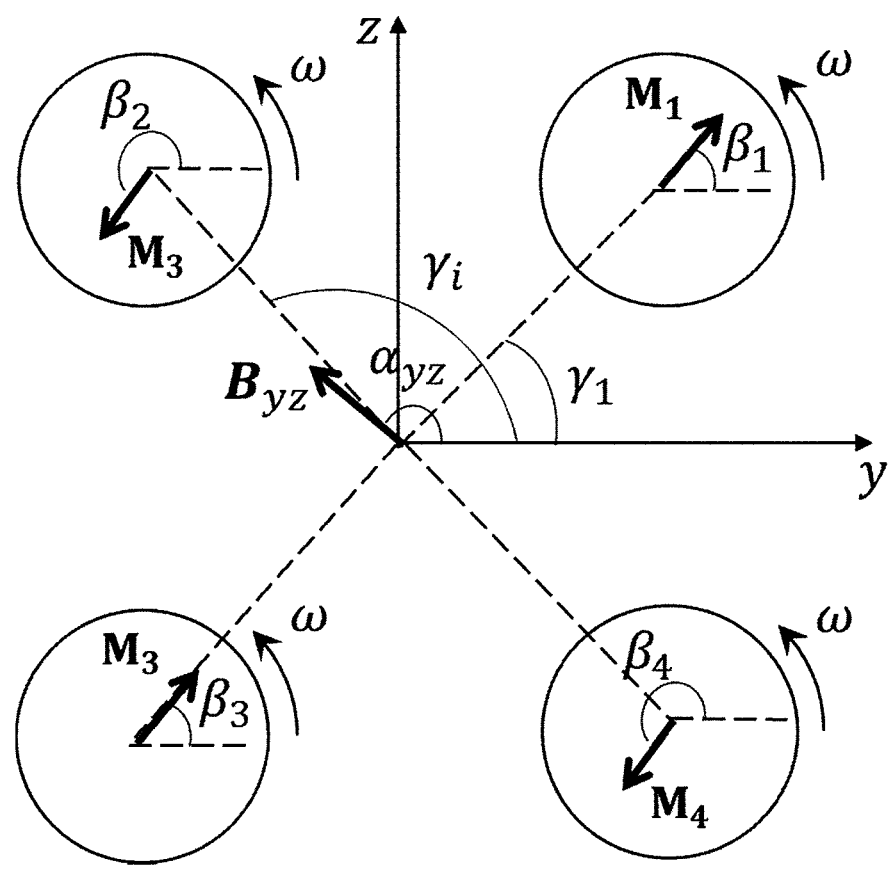
FIG. 11 A cross-sectional view in the yz-plane through a group of four permanent magnets that gives rise to a magnetic field $B_{yz}$.

With the solved angles in each direction $\alpha$ . . . , the angle of each magnet 1 in the group can be calculated using the following method. Considering the cross section of each group, eg with four permanent magnets 1 (n=4) in one group is illustrated in FIG. 11. In this embodiment, each magnet 1 rotates about an axis (the x axis in this case) that is orthogonal to its magnetic moment with the same angular velocity $\omega$. The rotation angle of the ith magnet $\beta_i$ follows the following relationship:

$$\beta_i\ldots=2\gamma_i-\alpha\ldots, i==1,2,3,4 \qquad (19)$$

where . . . should be substitute with xy, xz, or yz that stands for the directions, $\gamma_i$ is the angle between the line of magnet centre to workspace 3 centre and one axis (the y axis in the current embodiment).

Figure 12:
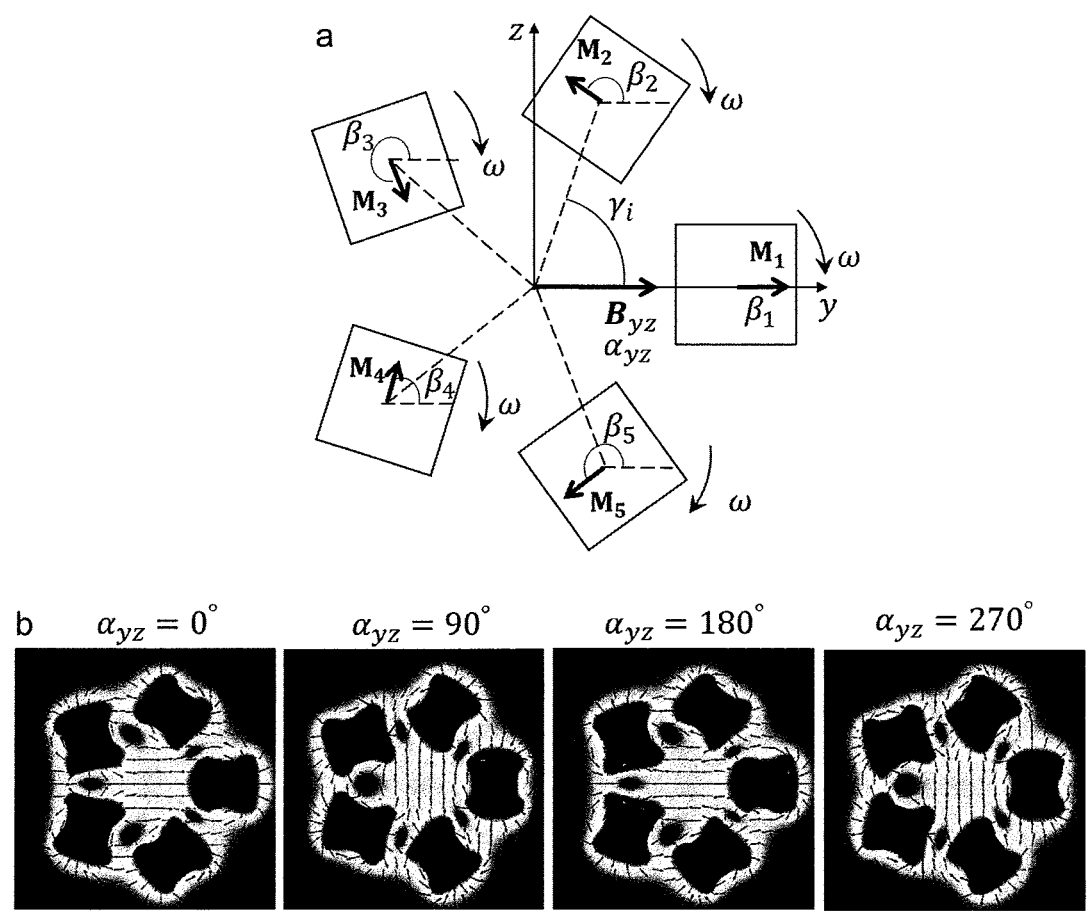
FIG. 12 A cross-section view in the yz-plane through a group of five permanent magnets that gives rise to a magnetic field $B_{yz}$ (a) in a schematic cross-sectional view (a) Schematic of the geometry; and (b) the results of a numerical simulation that verifies the rotating magnetic field; the arrows in the simulation point at the direction of the magnetic field and the lengths of the arrows correspond to the field strength.

The equation (19) is always valid, if the number of magnets 1 in each group is larger than or equal to two (n≥2), regardless the number of magnets 1 is an odd or even number. One embodiment with five magnets, which are 30 mm in side lengths and whose centre points are arranged on a circle of diameter 70 mm, is also shown as an example in FIG. 12. Using equation (19), the angle of each magnet is calculated, and the design is verified by the finite element simulation of the magnetic field (Comsol multiphysics 5.2a, Comsol). In FIG. 12b, a sequence of images show the simulation results in a step of 90°, that the resulting magnetic field 2 is temporally and spatially homogeneous in the workspace 3, and the field direction rotates counter-clockwise as the five magnets 1 are positioned at the right angles according to equation (19) and rotate clockwise.

Figure 13:
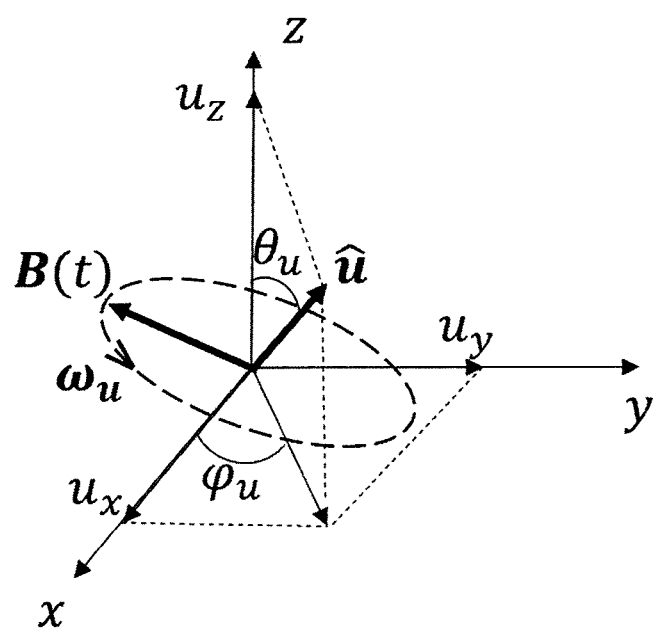
FIG. 13 An illustration of a magnetic field B rotating about an axis defined by vector û in tree-dimensional space.

In another embodiment, it is required to generate a rotating resulting magnetic field 2 that is spatially and temporally homogeneous in the field strength, and the field direction rotates around a defined axis in 3D. An illustrated in FIG. 13, the rotational axis is defined by the unity vector $\hat{u}$:

$$\hat{u}=[u_x,u_y,u_z]^T=[\sin\vartheta_u\cos\varphi_u, \sin\vartheta_u\sin\varphi_u, \cos\varphi_u]^T \quad (20)$$

The rotational magnetic field vector is a function of time:

$$B(t)=R(t)B_0=B_0R(t)\hat{v} \quad (21)$$

where $\hat{v}$ is the unity vector in the direction of the magnetic field B(t), and with a given initial value, $\hat{v}$ can be solved by the following equation:

$$\hat{u}\cdot\hat{v}=0 \quad (22)$$

R(t) is the rotational matrix around the axis $\hat{u}$ by an angle $\delta$:

$$R(t) = \begin{bmatrix} \cos\delta+u_x^2(1-\cos\delta) & u_xu_y(1-\cos\delta)-u_z\sin\delta & u_xu_z(1-\cos\delta)+u_y\sin\delta \\ u_xu_y(1-\cos\delta)+u_z\sin\delta & \cos\delta+u_y^2(1-\cos\delta) & u_yu_z(1-\cos\delta)-u_x\sin\delta \\ u_zu_x(1-\cos\delta)-u_y\sin\delta & u_zu_y(1-\cos\delta)+u_x\sin\delta & \cos\delta+u_z^2(1-\cos\delta) \end{bmatrix} \quad (23)$$

where $\delta=\omega_u t=2\pi f t$, in which $\omega_u$ is the angular velocity in the unit of rad/s, f is the rotational frequency in the unit of Hz, and t is time in the unit of second.

Figure 14:
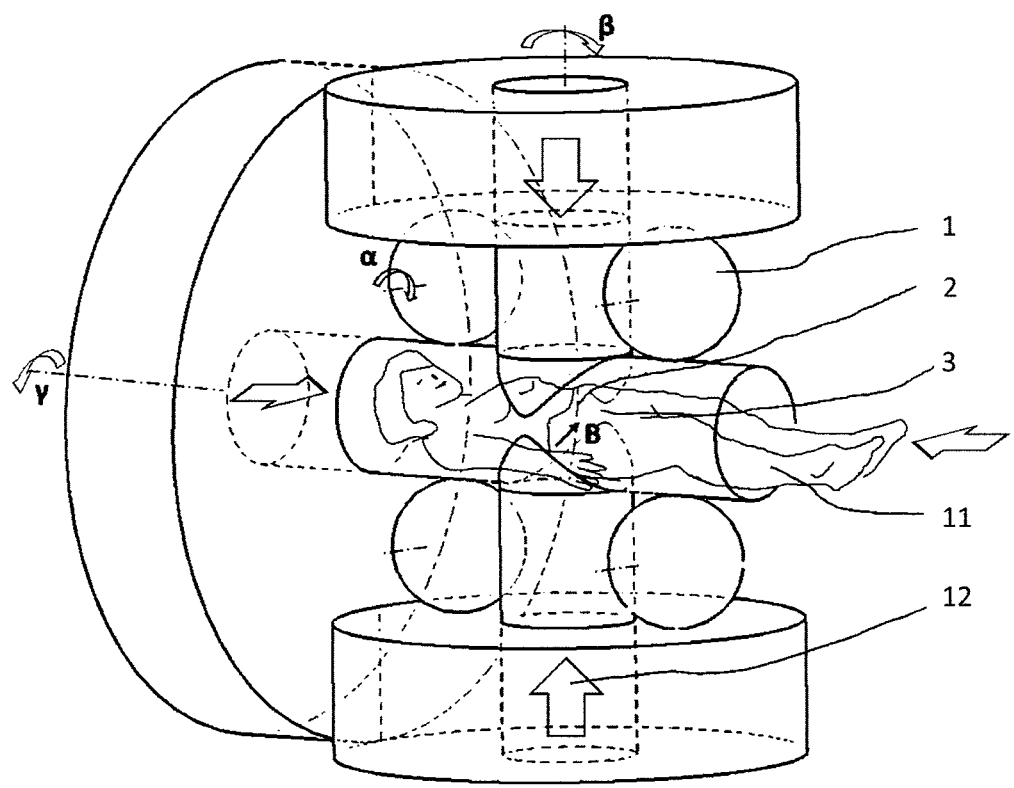
FIG. 14 A schematic perspective view of a magnetic field generator with one group of magnets used for medical applications.

Generating a Three-Dimensional Magnetic Field with One Group of Magnets on Rotational Stages One group of four magnets 1 is able to achieve an in-plane rotational magnetic field (as shown above in FIG. 3). To realize the three-dimensional steering of the rotational axis of the field, the magnets are mounted to a 2 DoF rotational stage (shown as the rings in FIG. 14). The stage rotates the whole setup (relative to the patient) in two directions, β and γ. The disadvantages of the embodiment are: 1) The access to the workspace is only limited to one direction, ie along the γ axis is permanent; however, access from other directions, eg along the β axis is blocked due to the rotation of the whole device; 2) The connections to drive the magnets 1 are cumbersome and expensive due to the rotation of the whole device; 3) The rotation of the whole device requires much higher power and is more dangerous to the patient 11 or the operator.

Figure 15:
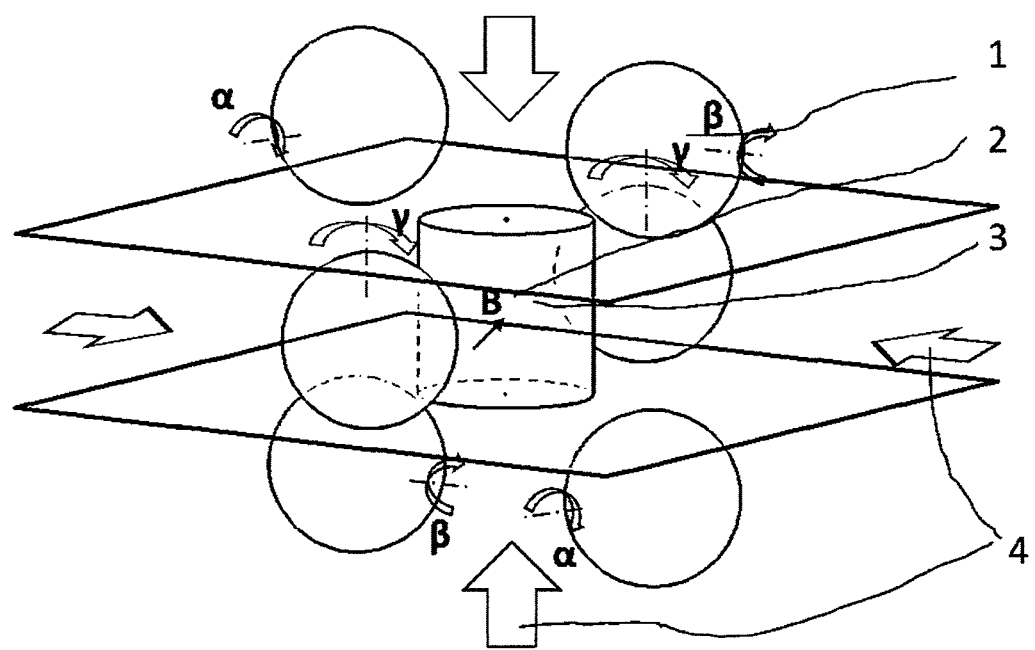
FIG. 15 A schematic perspective view of a magnetic field generator with six magnets arranged in in three groups with two magnets per group.

Example: Generating a Three-Dimensional Magnetic Field with Six Magnets that Each can Rotate in Two Directions As shown in FIG. 15, spherical permanent magnets 1 are arranged in three groups, and two magnets 1 in each group. The magnets 1 of each group simultaneously rotate with 2 DoF. It is also possible to achieve the full control of both the direction and the magnitude of the magnetic vector. Each magnet 1 (magnetic moment) can rotate around two orthogonal axes (two of the three axes, shown as α, β and γ).

Example: Experimental Methods of the Magnetic Generator

The magnetic set-up consists of four spherical magnets 1 with 30 mm diameter (K-30-C, neodymium N40, Supermagnete). They were held in spherical cavities in a custom-made coupler to connect to the motors. The orientation of the magnets 1 was maintained due to the large friction induced by the clamping force. Four stepper motors (1.8°/step, stall torque 0.15 N·m, SH3537-12U40, Sanyo Denki, not shown) were used with two individual driver boards (US1D200P10, 2.0 A, 16-division, Sanyo Denki, not shown) to drive the rotations in two directions, respectively. The power was supplied by a DC power supply (HM7042-5, HAMEG). The initial orientations $\alpha_0$ of the four magnets 1 were adjusted manually, then they were rotated with the same absolute speed, controlled by a square wave signal generated from a function generator (33220A, Agilent, not shown). The motors were air cooled with four fans (not shown), as heat was generated, especially when the motors were held in a fixed static position against the magnetic torque.

The diagonal centre-to-centre distances of the magnets 1 were set at 120 mm. Changing the distance between the magnets 1 will change the maximal magnetic field strength. Decreasing the distance will result in a larger field, however, it also requires larger driving torque by the motor, which then exceeds the stall torque of this motor for particular orientations of the magnets 1.

A digital gaussmeter (HGM09s, MAGSYS) was used to measure the resulting magnetic field 2 at the centre of the magnetic field generator in both the x and z directions, respectively. The field 2 was changed in steps of 22.5° (200 pulses) and the results are plotted as markers in FIG. 7. The measurements were repeated for three times. At the same position, the magnitudes were reproducible within ±0.5 G, so the error bars are not plotted in the figure.

The magnetic field strength and direction were also simulated in Comsol 5.2a (Comsol Multiphysics). A three-dimensional simulation was carried out in a volume of 300 mm-side cube using a magnetic insulation boundary condition. Four spherical magnets 1 with 30 mm diameter were placed with a diagonal centra-centre distance of 120 mm, as shown in FIG. 3a. The relative permeability of air and the four magnets 1 are set as 1 and 4000, respectively. The magnetization strength of each magnet was set to be 955 kA/m, and each orientation was calculated according to Equations 6 to 9. A parametric sweep was carried out for $\alpha_B=0°, 15°, 30°, 45°, 90°$, and $\beta=0°\sim360°$ in 10° steps. The magnetic flux density is shown by the grayscale, and the direction of the field is shown as arrows in FIG. 6.

Example: Multiple Magnets in One Group

In each group, there are at least two magnets 1 (arranged on opposing sides of the workspace); and there can be more than four magnets 1, as more magnets result in a higher flux density over a larger workspace 3. The mechanical driving mechanism (not shown) of the magnets 1 does not require the direct connection to a particular magnet 1, and can include a belt drive, a gear drive or any other suitable means of actuation.

Figure 16:
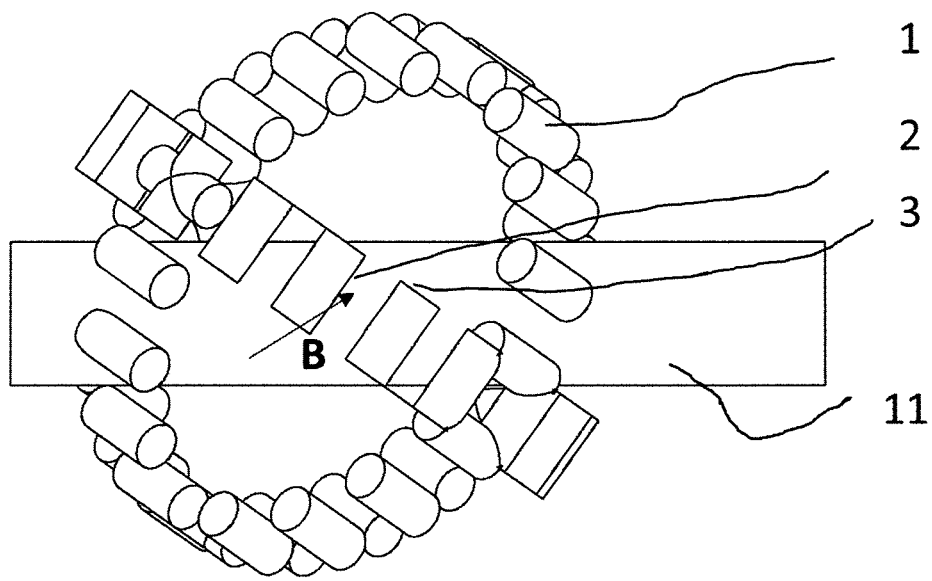
FIG. 16 A schematic perspective view of a human-scale magnetic field generator; top: side view, bottom: front view.
Figure 16:
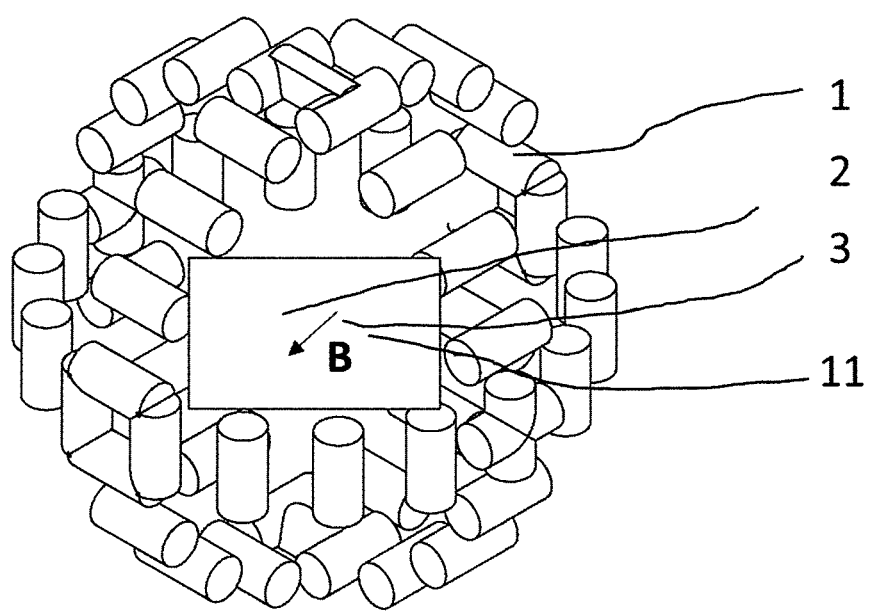

Each group of magnets 1 has plane and a hub and the magnets 1 are equidistantly in a circle. The hubs of the groups coincide with each other, and with the centre of the workspace 3. As shown in FIG. 16, the central symmetric axis of each group is perpendicular to that of another group, but it is not necessary to be perpendicular to the axis of the workspace 3 (the coordinate system of the patient in this case). Three groups the orientations of which are orthogonal to each other achieve full control of the direction and strength of the resulting magnetic field 2 in the workspace 3 by the disclosed method in the patent.

Figure 17:
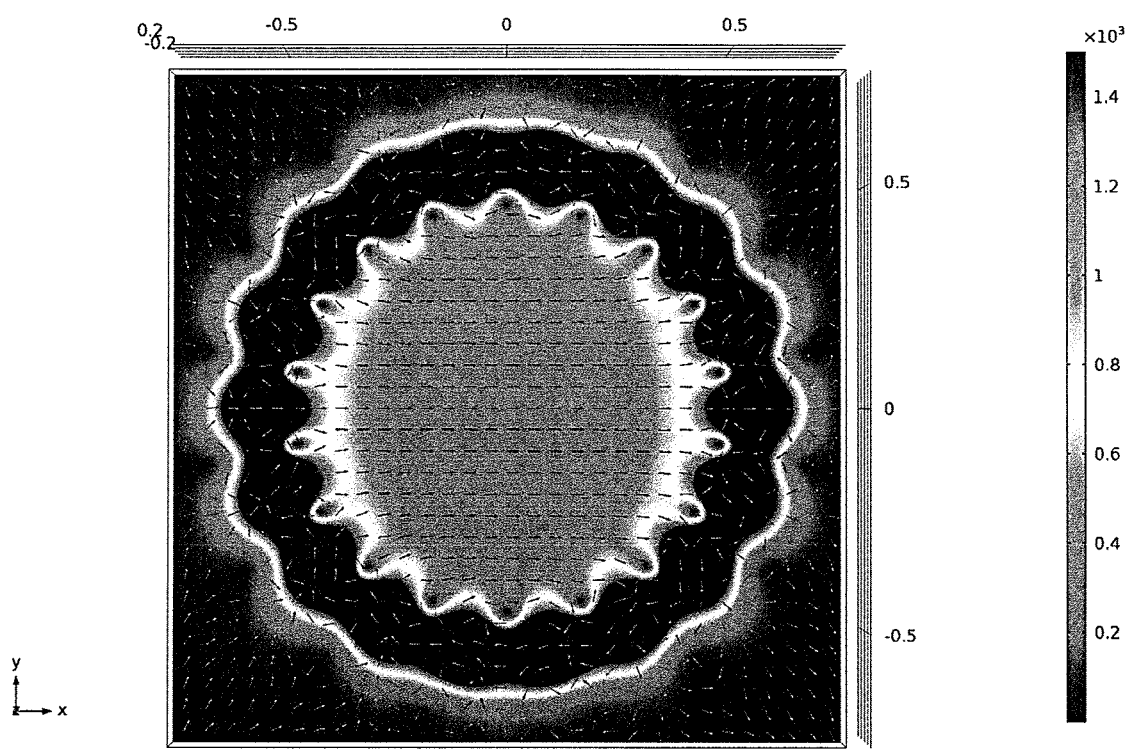
FIG. 17 The result of a finite element simulation of one group of 18 magnets in a human-scale setup; the arrows represent the direction of the magnetic field, and the grey tone represents the flux density; the length in the figure has a unit of meter and the grey tone scale has a unit of Gauss.

In one embodiment, the setup with multiple magnets 1 can be extended to human-scale, as shown in FIG. 16 and FIG. 17. In each group, there are 18 magnets 1 that are 100 mm in diameter and 200 mm in length. The inner diameter (gap) of each group is set to be 1000 mm, which fits a human through the opening space (access). The cuboid in FIGS. 16 and 17 represents the outer bounding box of a human, with a width of 500 mm, a thickness of 300 mm, and a length of 1700 mm. By finite element analysis of one group of 18 magnets with a coercive field strength of approximately 955 kA/m, the magnetic flux density is homogenous in the workspace and reaches approximately 448 Gauss.

Example: Powering a Linear Actuator with the Magnetic Field Generator

Figure 18:
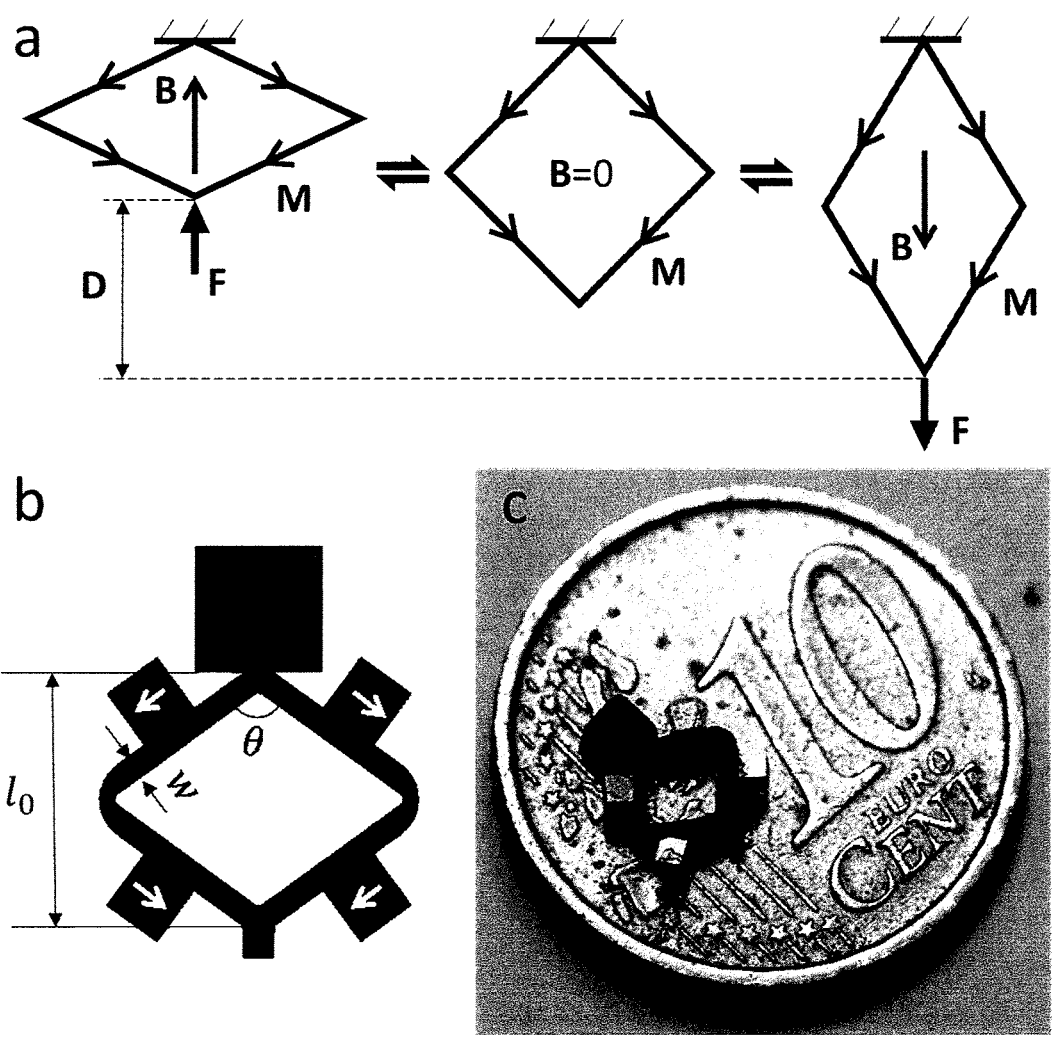
FIG. 18 A soft miniaturized linear actuators that is wirelessly powered by the magnetic field generator; (a) is a schematic representation of the working principle of the actuation; (b) is a drawing of the actuator where the arrows in the attached magnets indicate their magnetization, and (c) is a photograph of the assembled actuator on a 10-cent coin.
Figure 19:
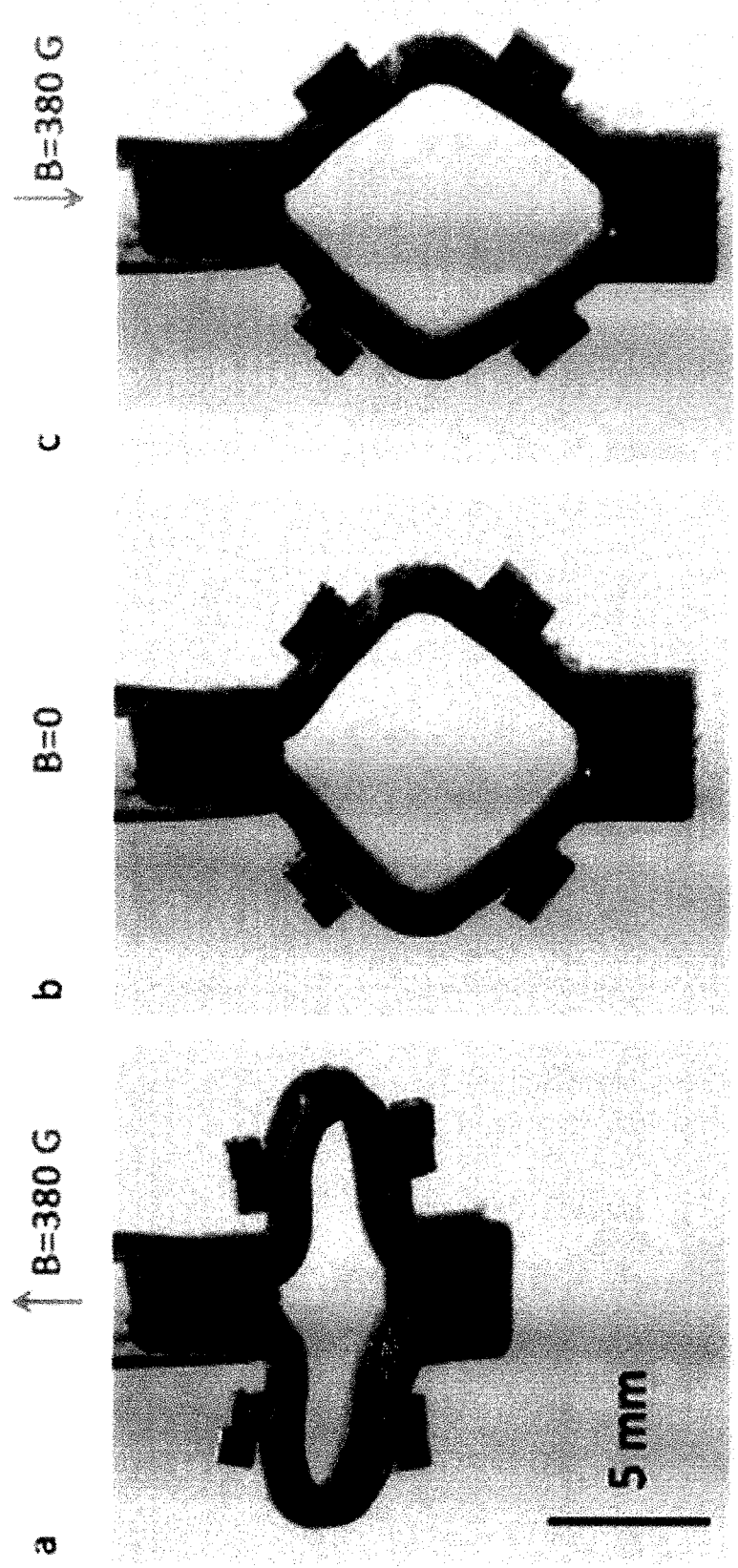
FIG. 19 Photographic snapshots of a video that shows the movement of the linear actuator of FIG. 1 when operated by a magnetic field generator; The snapshots show the compressed (a), relaxed (b) and elongated (c) states of the soft actuator.

As one application of the oscillating magnetic field generated by the device, a linear actuator was powered wirelessly, as shown in FIG. 18*a*. When the external field equals to zero, the soft structure stays at rest in its original shape (FIG. 18*b*). When a magnetic field in the z direction is applied, magnetic torques are applied on the embedded small magnets, which result in the rotation of the soft linkages and compress the actuator (FIG. 18*a*). The actuator with an original length $l_0$=8.8 mm decreases to a minimal length of l=3.7 mm. When a magnetic field is applied in the opposite direction, it extends to l=10.5 mm. Thus an overall linear displacement of approximately 6.8 mm is realized by the actuator without external load, which is more than 70% of its original length. The displacement at compression (5.1 mm) is much larger than at elongation (1.7 mm), as the magnetic torque changes non-linearly with the orientation of the magnets, and it is maximal when the angle is 90° (close to the situation shown in FIG. 19).

Figure 20:
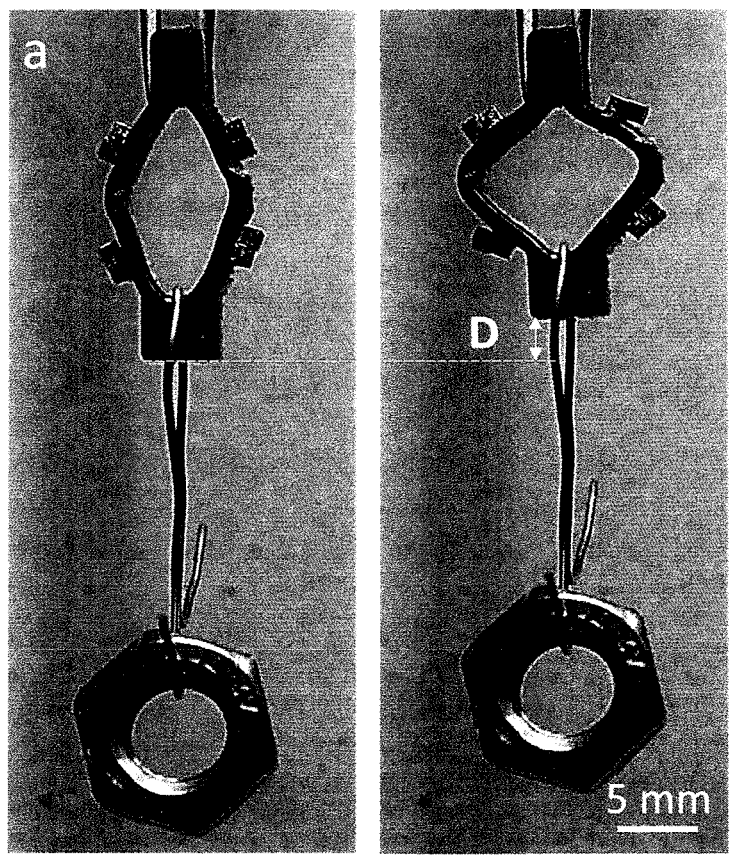
FIG. 20 The results of load measurements on the linear actuator of FIGS. 18 and 19; (a) shows a snapshots of the video showing the lift of a load by the actuator powered by the magnetic field generator; and (b) shows the maximal displacement D of the actuator plotted against different loads L and the work W calculated from the load and the displacement.
Figure 20:
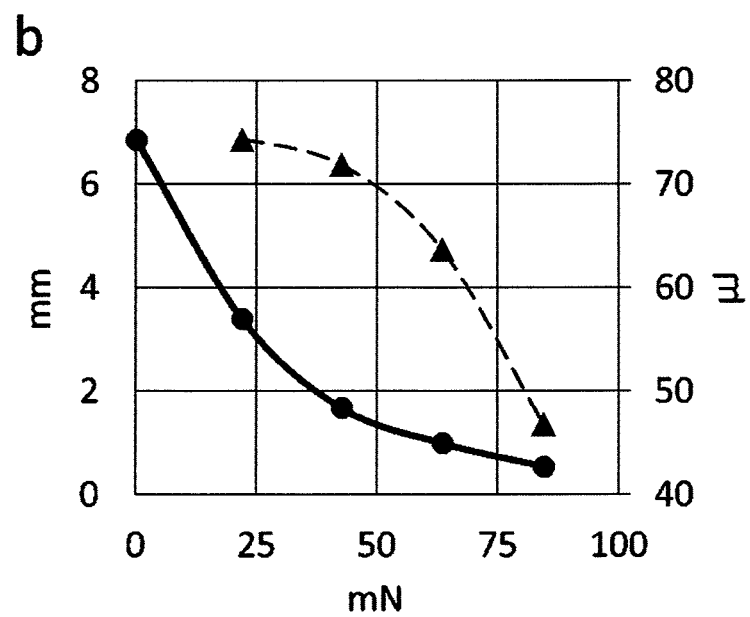

The load characteristics of the actuator was also tested. The maximal displacement is plotted as a function of the external load in FIG. 20*b*. As the load increases, the displacement decreases non-linearly due to the variance in the orientation of the magnets. The output work of the actuator also drops dramatically as the displacement gets smaller. Further optimization of the structure and matching the soft material's elastic modulus with the load will enhance the performance of the actuator. The current miniature actuator can provide a maximal force of approximately 84 mN. It lifts more than 40 times of its own weight, while still achieving 10% displacement. It is also worthwhile to point out, as the soft structure is planar, it is fully compatible with traditional soft photolithography process, and thus it can be scaled down to the micrometre scale.

The features as described in the above description, claims and figures can be relevant individually or in any combination to realise the various embodiments of the invention.

The invention claimed is:

1. A magnetic field generator that comprises at least three groups of magnets, the magnetic moment of each magnet being rotatable about a rotation axis, wherein each group comprises at least three magnets, and each group has an orientation in the sense that the rotation axes of the magnetic moments of the magnets of the same group extend in the group's orientation, wherein the orientations of the different groups are linearly independent.

2. The magnetic field generator of claim 1, wherein the magnets are permanent magnets.

3. The magnetic field generator of claim 1, wherein the magnetic moment of at least one magnet forms an angle of more than 80 degrees with the orientation of the rotation axis.

4. The magnetic field generator of claim 1, wherein in at least one group of magnets has a hub in the sense that all magnets of this group have the same distance to the group's hub.

5. The magnetic field generator of claim 1, wherein the maximum achievable flux density of the resulting magnetic field generated in a workspace by the magnets in combination in each one of the achievable orientations of the resulting magnetic field is larger than 90 Gauss.

6. The magnetic field generator of claim 1, wherein by mean of rotating the magnetic moment(s) of one or more of the magnets a spatial gradient of the magnetic flux density of the magnetic field generated in a workspace by the magnets in combination can be changed.

7. The magnetic field generator of claim 1, wherein the direction of the resulting magnetic field can be changed at a speed larger than 0.1 degrees per second.

8. A method of changing at least one property of a resulting magnetic field generated by at least three groups of magnets by means of rotating the magnetic moment of each magnet about a rotation axis, wherein each group comprises at least three magnets, and wherein each group has an orientation in the sense that the rotation axes of the magnetic moments of the magnets of the same group extend in the group's orientation, wherein the orientations of the different groups are linearly independent.

9. Use of the magnetic field generator according to claim 1 for actuating a tethered or untethered device that possesses a magnetic moment.

10. Use of the method according to claim 8 for actuating a tethered or untethered device that possesses magnetic moment.

\* \* \* \* \*

UNITED STATES PATENT AND TRADEMARK OFFICE
CERTIFICATE OF CORRECTION

PATENT NO. : 12,257,016 B2
APPLICATION NO. : 17/054779
DATED : March 25, 2025
INVENTOR(S) : Tian Qiu and Peer Fischer Page 1 of 1

It is certified that error appears in the above-identified patent and that said Letters Patent is hereby corrected as shown below:

In the Specification

In Column 3, Line 4, "an" should read "a";

In Column 3, Line 7, "according to claim 9" should read "according to claim 8";

In Column 3, Lines 16-17, "according to claim 2. The magnetic field generator" should read "that";

In Column 4, Lines 17-18, "with the features of claim 3. The magnetic field generator" should read "that";

In Column 4, Lines 48-49, "with the features of claim 4. The magnetic field generator" should read "that".

Signed and Sealed this
Seventeenth Day of June, 2025

Coke Morgan Stewart
*Acting Director of the United States Patent and Trademark Office*